(12) United States Patent
Hsia et al.

(10) Patent No.: US 11,491,115 B2
(45) Date of Patent: Nov. 8, 2022

(54) NANOPARTICLES CONTAINING EXTRACELLULAR MATRIX FOR DRUG DELIVERY

(71) Applicant: The Board of Regents of the University of Texas System, Austin, TX (US)

(72) Inventors: Connie Hsia, Dallas, TX (US); Yi Hong, Irving, TX (US); Orson W. Moe, Dallas, TX (US); Kytai Nguyen, Grand Prairie, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 16 days.

(21) Appl. No.: 15/742,842

(22) PCT Filed: Jul. 8, 2016

(86) PCT No.: PCT/US2016/041516
§ 371 (c)(1),
(2) Date: Jan. 8, 2018

(87) PCT Pub. No.: WO2017/008016
PCT Pub. Date: Jan. 12, 2017

(65) Prior Publication Data
US 2018/0207107 A1    Jul. 26, 2018

Related U.S. Application Data

(60) Provisional application No. 62/190,591, filed on Jul. 9, 2015.

(51) Int. Cl.
*A61K 9/51* (2006.01)
*A61K 9/00* (2006.01)
(Continued)

(52) U.S. Cl.
CPC .......... *A61K 9/5176* (2013.01); *A61K 9/0019* (2013.01); *A61K 9/0078* (2013.01);
(Continued)

(58) Field of Classification Search
None
See application file for complete search history.

(56) References Cited

U.S. PATENT DOCUMENTS

2008/0095860 A1    4/2008  Firestone
2009/0138074 A1    5/2009  Freyman et al.
(Continued)

FOREIGN PATENT DOCUMENTS

WO     WO 2007/011644      1/2007
WO     WO-2013120082 A1 *  8/2013  ............. A61L 31/08

OTHER PUBLICATIONS

M Shevach, S Fleischer, A Shapira, T Dvir. "Gold Nanoparticle-Decellularized Matrix Hybrids for Cardiac Tissue Engineering." Nano Letters, vol. 14, 2014, pp. 5792-5796. (Year: 2014).*
(Continued)

*Primary Examiner* — Isaac Shomer
(74) *Attorney, Agent, or Firm* — Parker Highlander PLLC

(57) ABSTRACT

Nanoparticles coated with extracellular matrix (ECM) are provided, in some aspects, for the delivery of a therapeutic protein, nucleic acid, or drug. In some embodiments, the nanoparticles are delivered to a subject via inhalation or aerosol delivery. Also provided, in some aspects, are methods for treating acute lung injury comprising administering α-Klotho (αKlotho) protein or DNA to a subject.

12 Claims, 15 Drawing Sheets

Specification includes a Sequence Listing.

(51) Int. Cl.
  *A61P 11/00* (2006.01)
  *A61K 31/713* (2006.01)
  *A61K 38/47* (2006.01)
(52) U.S. Cl.
  CPC .......... *A61K 9/5153* (2013.01); *A61K 31/713* (2013.01); *A61K 38/47* (2013.01); *A61P 11/00* (2018.01); *C12Y 302/01031* (2013.01)

(56) References Cited

U.S. PATENT DOCUMENTS

| | | | | |
|---|---|---|---|---|
| 2009/0192087 | A1* | 7/2009 | Glass | C12N 9/2402 435/325 |
| 2010/0285111 | A1* | 11/2010 | Ko | A61P 43/00 424/450 |
| 2011/0045045 | A1* | 2/2011 | Cortiella | A61K 35/42 424/422 |
| 2013/0337066 | A1* | 12/2013 | Zhang | A61K 39/0011 424/489 |
| 2014/0287049 | A1 | 9/2014 | Bilgicer et al. | |
| 2017/0226172 | A1* | 8/2017 | Mohammadi | C07K 14/50 |

OTHER PUBLICATIONS

J Menon, p. RAvikumar, A Pise, D Gyawali, CCW Hsia, KT Nguyen. "Polymeric nanoparticles for pulmonary protein and DNA delivery." Acta Biomaterialia, vol. 10, 2014, pp. 2643-2652, available online Feb. 8, 2014. (Year: 2014).*
P Ravikumar, J Ye, J Zhang, SN Pinch, MC Hu, M Kuro-o, CCW Hsia, OW Moe. "a-Klotho protects against oxidative damage in pulmonary epithelia." American Journal of Physiologicaly Lung Cellular and Molecular Physiology, vol. 307, 2014, pp. L566-L575. (Year: 2014).*
H Patel, H Xu, S-H Su, C Patterson. "Optimization of Extracellular Matrix Protein Surface Coating to Enhance Endothelialization on Poly(L-Lactic Acid)." IEEE, ISBN 978-1-4244-1626-4, 2004, pp. 27-30. (Year: 2007).*
JD O'Neill et al. "Decellularization of Human and Porcine Lung Tissues for Pulmonary Tissue Engineering." Annals of Thoracic Surgery, vol. 96, 2013, pp. 1046-1056. (Year: 2013).*
J Zhang, K Cao, JV Pastor, L Li, OW Moe, CCW Hsia. "Alpha-Klotho, a critical protein for lung health, is not expressed in normal lung." FASEB BioAdvances, vol. 1, 2019, pp. 675-687. (Year: 2019).*
M Ackermann et al. "Pulmonary Vascular Endothelialitis, Thrombosis, and Angiogenesis in Covid-19." published May 21, 2020, pp. 1-9. (Year: 2020).*
Y Saito et al. "In Vivo klotho Gene Delivery Protects against Endothelial Dysfunction in Multiple Risk Factor Syndrome." vol. 276, 2000, pp. 767-772. (Year: 2000).*
H Mitani et al. "In Vivo klotho Gene Transfer Ameliorates Angiotensin II—Induced Renal Damage." Hypertension, vol. 39, 2002, pp. 838-843. (Year: 2002).*
Shane Browne, Gianluca Fontana, Brian J. Rodriguez, and Abhay Pandit. "A Protective Extracellular Matrix-Based Gene Delivery Reservoir Fabricated by Electrostatic Charge Manipulation." Molecular Pharmaceutics, vol. 9, 2012, pp. 3099-3106. (Year: 2012 ).*
Maytal Bivas-Benita, Stefan Romeijn, Hans E. Junginger, Gerrit Borchard. "PLGA-PEI nanoparticles for gene delivery to pulmonary epithelium." European Journal of Pharmaceutics and Biopharmaceutics, vol. 58 (2004), pp. 1-6. (Year: 2008).*
Hiromi Rakugi et al. "Anti-oxidative effect of Klotho on endothelial cells through cAMP activation." Endocrinology, vol. 31, 2007, pp. 82-87. (Year: 2007).*
Gerd P Pfeifer et al. "Tobacco smoke carcinogens, DNA damage and p53 mutations in smoking-associated cancers." Oncogene, vol. 21, 2002, pp. 7435-7451. (Year: 2002).*

M. Drent et al. "Usefulness of lactate dehydrogenase and its isoenzymes as indicators of lung damage or inflammation." European Respiratory Journal, vol. 9, 1996, pp. 1736-1742. (Year: 1996).*
Makoto Kuro-o et al. "Mutation of the mouse klotho gene leads to a syndrome resembling ageing." Nature, vol. 390, Nov. 6, 1997, pp. 45-51. (Year: 1997).*
M Mouded et al. "Epithelial Cell Apoptosis Causes Acute Lung Injury Masquerading as Emphysema." American Journal of Respiratory Cell and Molecular Biology, vol. 41, 2009, pp. 407-414. (Year: 2009).*
Ahmed et al., "Reduction in burst release after coating poly (D, L-lactide-co-glycolide)(PLGA) microparticles with a dmg-free PLGA layer," *Pharm. Dev. Technol.*, 17(1):66-72, 2012.
Azarmi et al., "Targeted delivery of nanoparticles for the treatment of lung diseases," *Adv. DrugDeliv. Rev.*, 60(8): 863-75, 2008.
Barker et al., "The demonstration of αKlotho deficiency in human chronic kidney disease with a novel synthetic antibody," *Nephrol. Dial. Transplant.*, 30(2):223-233, 2015.
Booth et al., "Tissue engineering of cardiac valve prostheses I: development and histological characterization of an acellular porcine scaffold," *J. Heart Valve Dis.*, 11 (4): 457-62, 2002.
Danhier et al., "PLGA-based nanoparticles: an overview of biomedical applications," *J. Control. Release*, 161(2): 505-522, 2012.
Doi et al., "Lung injury following acute kidney injury: kidney—lung crosstalk," *Clin. Exp. Nephrol.*, 15(4):464-470, 2011.
Enayati et al., "Modification of the release characteristics of estradiol encapsulated in PLGA particles via surface coating," *Ther. Deliv.*, 3(2):209-226, 2012.
Faubel, "Pulmonary complications after acute kidney injury," *Adv. Chronic Kidney Dis.*, 15(3):284-296, 2008.
Fields et al., "Surface modified poly(β amino ester)-containing nanoparticles for plasmid DNA delivery", *J. Control. Release*, 164(1):41-48, 2012.
Fontana et al., "Amoxicillin-loaded polyethylcyanoacrylate nanoparticles: influence of PEG coating on the particle size, drug release rate and phagocytic uptake", *Biomaterials*, 22(21)2857-2865, 2001.
Gao et al., "TRPM2 mediates ischemic kidney injury and oxidant stress through RAC1," *J. Clin. Invest.*, 124(11),4989-5001, 2014.
Gazdhar et al., "Alpha-Klotho in induced pluripotent stem cell secretome contributes to antioxidation and lung protection," *Stem Cells*, 36:616-625, 2018.
Gibson et al., "Tissue Extracellular Matrix Nanoparticle Presentation in Electrospun Nanofibers," *Biomed. Res. Int.*, 2014: 469120, 2014.
Hsia et al., "Acute lung injury complicating acute kidney injury: A model of endogenous alphaKlotho deficiency and distant organ dysfunction," *Bone*, 100:100-9, 2017.
Hu et al., "Renal Production, Uptake, and Handling of Circulating alphaKlotho," *J. Am. Soc. Nephrol.*, 27: 79-90, 2016.
Hu et al., "Fibroblast growth factor 23 and Klotho: physiology and pathophysiology of an endocrine network of mineral metabolism," *Annu. Rev. Physiol.*, 75:503-533, 2013.
Hu et al., "Klotho and chronic kidney disease," *Adv. Exp. Med. Biol.*, 728:126-157, 2012.
Hu et al., "Klotho and phosphate are modulators of pathologic uremic cardiac remodeling," *J. Am. Soc. Nephrol.*, 26(6): 1290-1302, 2015.
Hu et al., "Klotho: a novel phosphaturic substance acting as an autocrine enzyme in the renal proximal tubule," *FASEB J.*, 24(9):3438-3450, 2010.
Hu et al., "Recombinant alpha-Klotho may be prophylactic and therapeutic for acute to chronic kidney disease progression and uremic cardiomyopathy," *Kidney Int.*, 91:1104-1114, 2017.
Hu et al., "Renal and extrarenal actions of Klotho," *Semin Nephrol.*, 33(2):118-129, 2013.
Hu et al., "The erythropoietin receptor is a downstream effector of Klotho-induced cytoprotection," *Kidney Int.*, 84(3): 468-481, 2013.
Imura et al., "Secreted Klotho protein in sera and CSF: implication for post-translational cleavage in release of Klotho protein from cell membrane," *FEBS Lett.*, 565:143-147, 2004.

(56) References Cited

OTHER PUBLICATIONS

International Preliminary Report on Patentability issued in corresponding PCT Application No. PCT/US2016/041516, dated Jan. 18, 2018.
International Search Report and Written Opinion issued in corresponding PCT Application No. PCT/US2016/041516, dated Nov. 15, 2016.
Iyer et al., "Nano-therapeutics for the lung: State of the art and future perspectives," *Curr. Pharm. Des.*, 21(36):5233-5244, 2015.
Kasuno et al., "Renal redox dysregulation in AKI: application for oxidative stress marker of AKI," *Am. J. Physiol. Renal Physiol.*, 307(12):F1342-F1351, 2014.
Ku et al., "Size Dependent Interactions of Nanoparticles with Lung Surfactant Model Systems and the Significant Impact on Surface Potential," *J. Nanosci. Nanotechnol.*, 8(6):2971-2978, 2008.
Kuro-o et al., "Mutation of the mouse klotho gene leads to a syndrome resembling ageing," *Nature*, 390(6655):45-51, 1997.
Matsumura et al., "Identification of the HumanKlothoGene and Its Two Transcripts Encoding Membrane and SecretedKlothoProtein," *Biochem. Biophys. Res. Commun.*, 242(3):626-630, 1998.
Medberry et al., "Hydrogels derived from central nervous system extracellular matrix," *Biomaterials*, 34(4):1033-40, 2013.
Menon et al., "Effects of surfactants on the properties of PLGA nanoparticles," *J. Biomed. Mater. Res. Part A*, 100(8):1998-2005, 2012.
Menon et al., "Polymeric nanoparticles for pulmonary protein and DNA delivery," *Acta Biomaterialia*, 10:2643-2652, 2014.
Murray and Lopez, "Alternative projections of mortality and disability by cause 1990-2020: Global Burden of Disease Study," *Lancet*, 349(9064):1498-504, 1997.
Nath and Norby, "Reactive oxygen species and acute renal failure," *Am. J. Med.*, 109(8):665-678, 2000.
Panesso et al., "Klotho has dual protective effects on cisplatin-induced acute kidney injury," *Kidney Int.*, 85(4):855-870, 2014.
Rabe et al.,*Am. J. Respir. Crit. Care Med.*, 176(6):532-55, 2007.
Ravikumar et al., "Alpha-Klotho deficiency in acute kidney injury contributes to lung damage", *J. Appl. Physiol.*, 120:72-732, 2016.
Ravikumar et al., "Alpha-Klotho protects against oxidative damage in pulmonary epithelia," *Am. J. Physiol. Lung Cell Mol. Physiol.*, 307:L566-75, 2014.
Ravikumar et al., "Nanoparticle facilitated inhalational delivery of erythropoietin receptor cDNA protects against hyperoxic lung injury," *Nanomedicine*, 12:811-821, 2016.
Rees et al. "The importance of particle size in response to inhaled bronchodilators," *Eur. J. Respir. Dis.*, 63(Suppl): 73-78, 1982.
Rubenfeld et al., "Incidence and outcomes of acute lung injury," *New Engl. J. Med.*, 353:1685-93, 2005.
Sawkins et al., "Hydrogels derived from demineralized and decellularized bone extracellular matrix," *Acta Biomater.*, 9(8):7865-7873, 2013.
Seif-Naraghi et al., "Safety and Efficacy of an Injectable Extracellular Matrix Hydrogel for Treating Myocardial Infarction," *Sci. Transl. Med.*, 5(173):173ra25, 2013.
Shi et al., "alphaKlotho Mitigates Progression of AKI to CKD through Activation of Autophagy," *J. Am. Soc. Nephrol.*, 27: 2331-2345, 2015.
Sokocevic et al. "The effect of age and emphysematous and fibrotic injury on the re-cellnlarization of de-cellularized lungs," *Biomaterials*, 34:3256-3269, 2013.
Suga et al., "Disruption of the klotho Gene Causes Pulmonary Emphysema in Mice: Defect in Maintenance of Pulmonary Integrity during Postnatal Life," *Am. J. Respir. Cell Mol. Biol.*, 22(1):26-33, 2000.
Sung et al., "Nanoparticles for drug delivery to the lungs," *Trends Biotechnol.*, 25(12): 563-570, 2007.
Tsushima et al., "Acute lung injury review," *Internal Med.*, 48(9):621-30, 2009.
Wolf et al., "A hydrogel derived from decellularized dermal extracellular matrix," *Biomaterials*, 33(29):7028-7038, 2012.
Wu et al. "An injectable extracellular matrix derived hydrogel for meniscus repair and regeneration," *Acta Biomater.*, 16:49-59, 2015.
Wu et al., "Lung protection by inhalation of exogenous solubilized extracellular matrix," *PLoS One*, 12(2):e0171165, 2017.
Zanen et al., "Optimal particle size for beta 2 agonist and anticholinergic aerosols in patients with severe airflow obstruction," *Thorax*, 51: 977-980, 1996.
Zanen et al., "The optimal particle size for β-adrenergic aerosols in mild asthmatics," *Int. J. Pharm.*, 107:211-217, 1994.
Cartotto et al., "The Acute Respiratory Distress Syndrome (ARDS) in mechanically ventilated burn patients: An analysis of risk factors, clinical features, and outcomes using the Berlin ARDS definition," *Burns*, 42:1423-1432, 2016.
De Jong et al., "Feasibility and effectiveness of prone position in morbidly obese patients with ARDS: a case-control clinical study," *Chest*, 143:1554-1561, 2013.
Rouby et al., "Regional distribution of gas and tissue in acute respiratory distress syndrome. II. Physiological correlations and definition of an ARDS Severity Score. CT Scan ARDS Study Group," *Intensive Care Med*, 26:1046-1056, 2000.
Siddiqi et al., "COVID-19 illness in native and immunosuppressed states: A clinical-therapeutic staging proposal," *J Heart Lung Transplant*, 39:405-407, 2020.
Faux et al., "The role of oxidative stress in the biological responses of lung epithelial cells to cigarette smoke," *Biomarkers*, 14(Suppl. 1):90-96, 2009.
Lubos et al., "Role of oxidative stress and nitric oxide in atherothrombosis," *Frontiers in Bioscience*, 13:5323-5344, 2008.
Wei et al., "Nitric oxide induces oxidative stress and apoptosis in neuronal cells," *Biochimica et Biophysica Acta*, 1498:72-79, 2000.

\* cited by examiner

A
| ECM concentration for coating | Coated NP Size (nm) | |
|---|---|---|
| | Adsorption coating | LBL coating |
| 100 μg/ml | 242 ± 97 | 399 ± 323 |
| 200 μg/ml | 226 ± 66 | 691 ± 366 |
| 300 μg/ml | 409 ± 209 | 385 ± 198 |
| 500 μg/ml | 301 ± 154 | 368 ± 191 |
| Coumarin-6 loaded PLGA NPs (uncoated) | 197 ± 41 | |
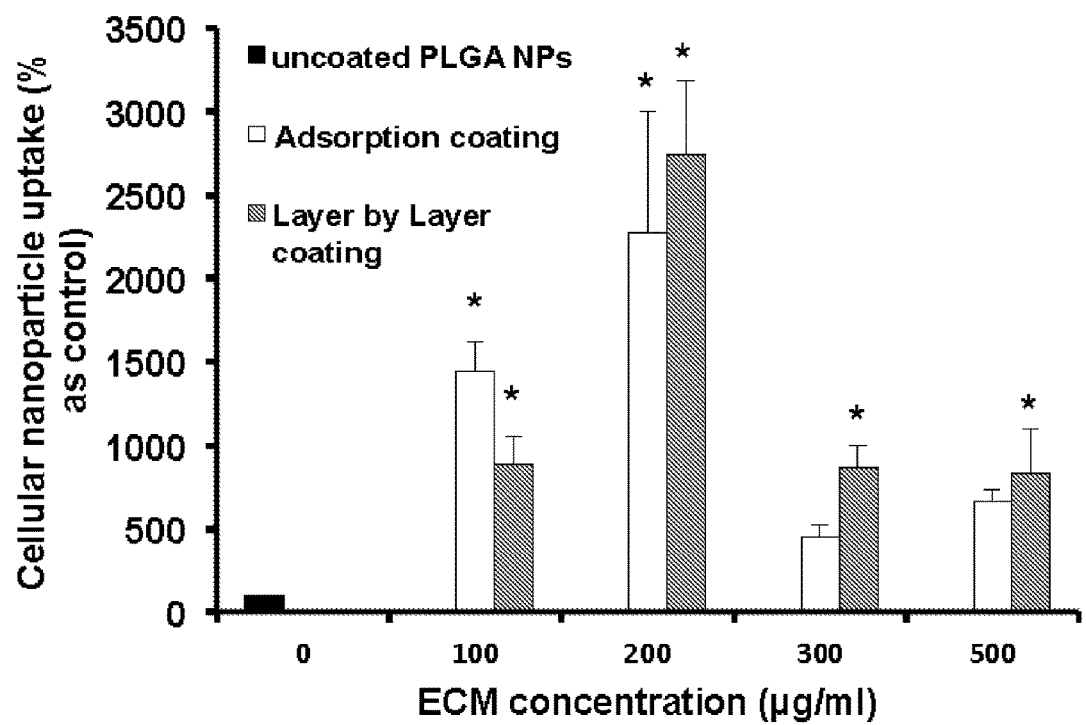
FIGS. 6A-B

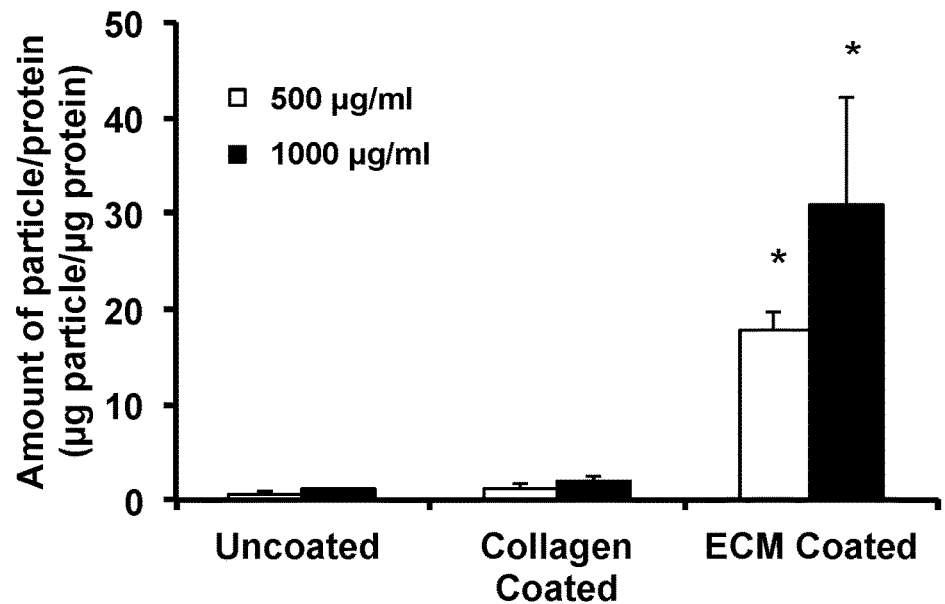
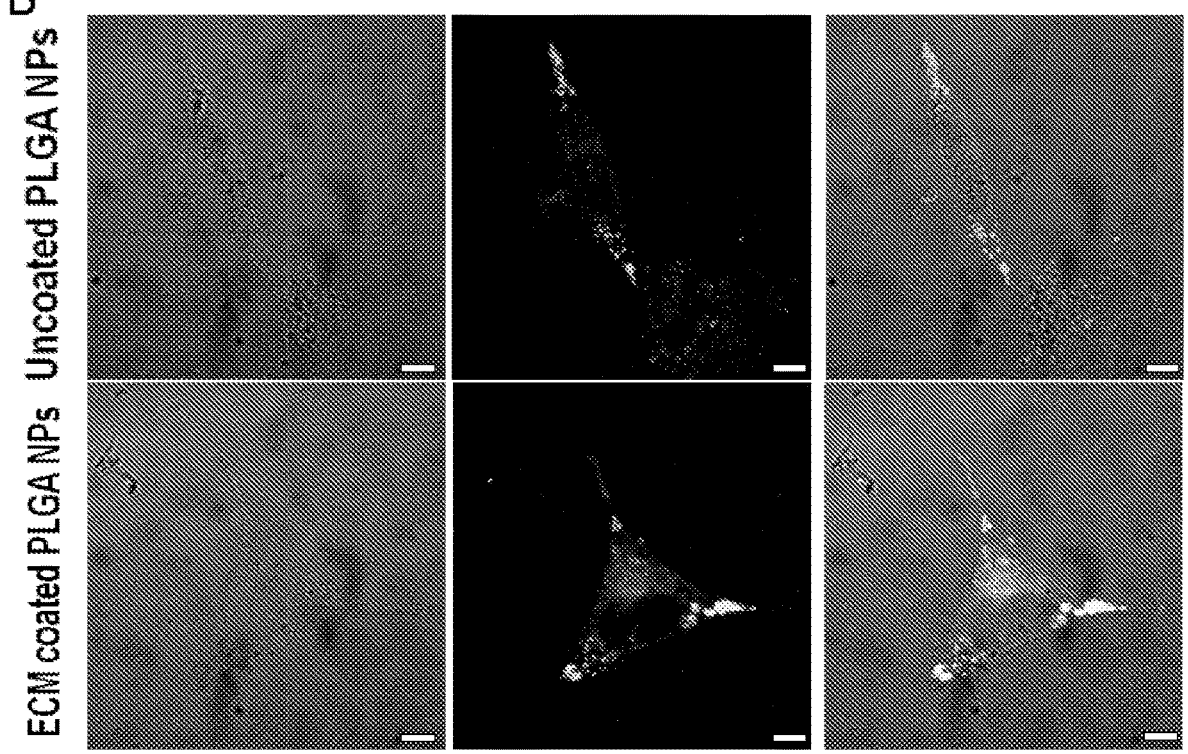
FIGS. 7A-B

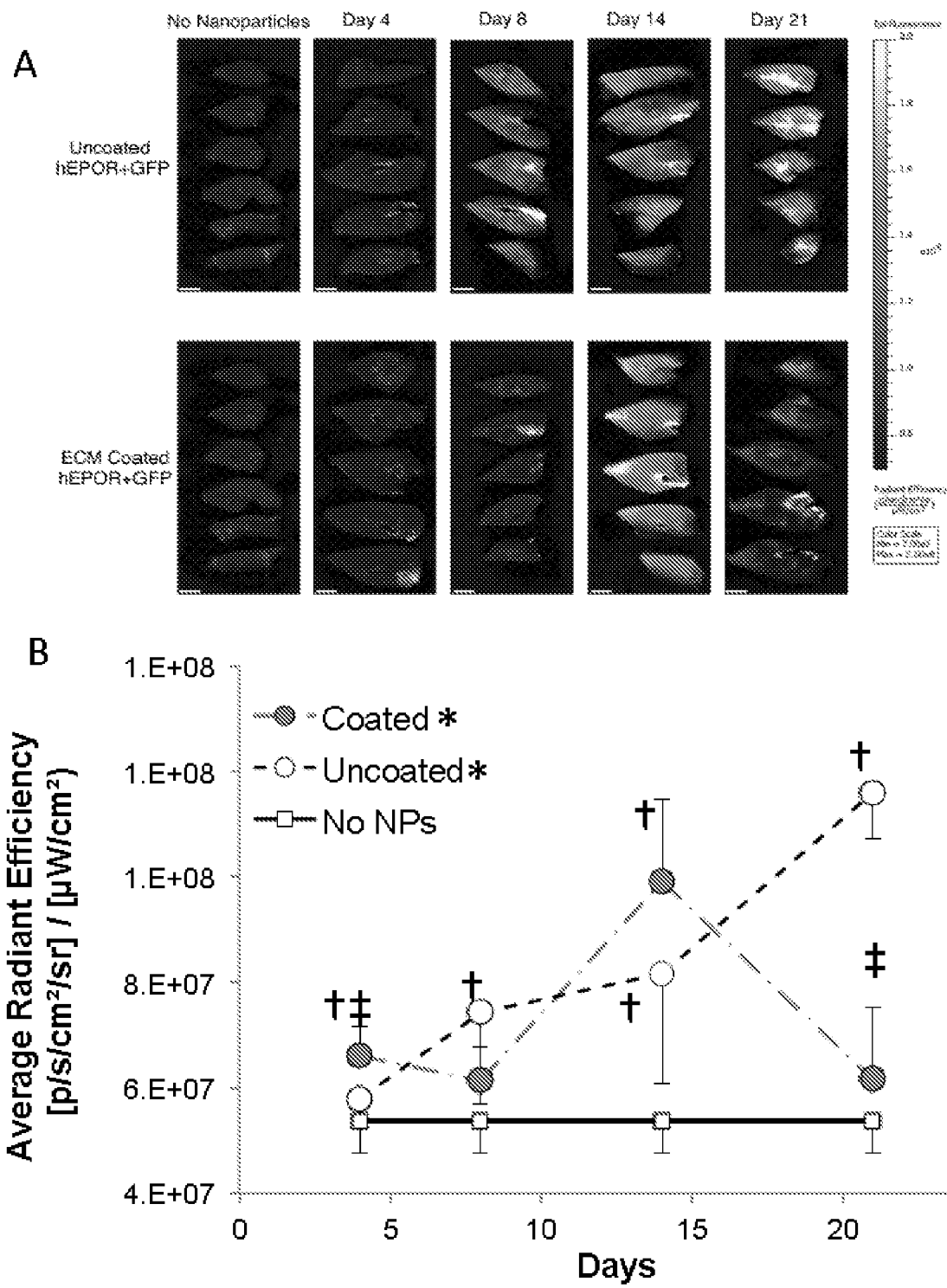
FIGS. 8A-B

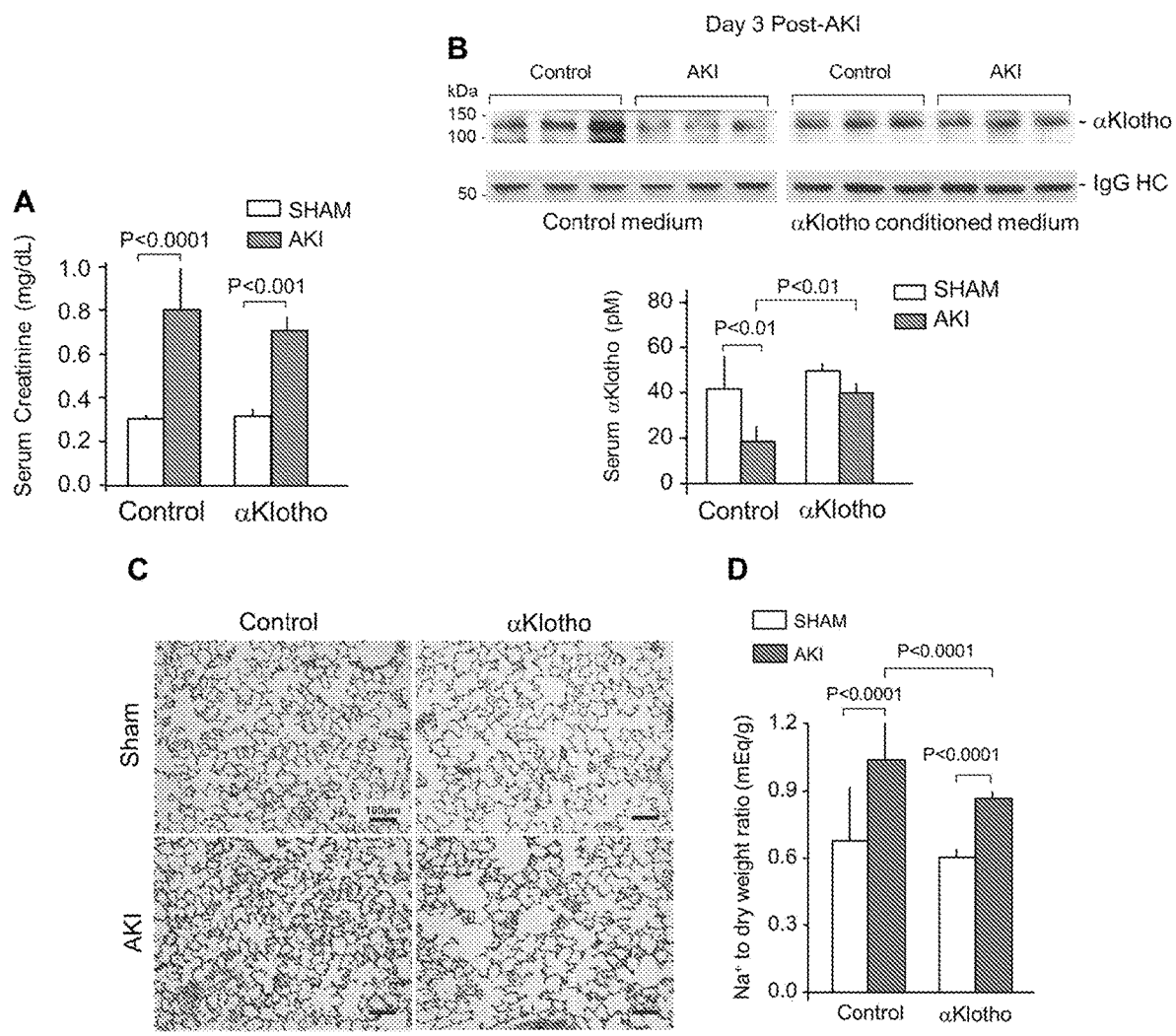
FIGS. 9A-D

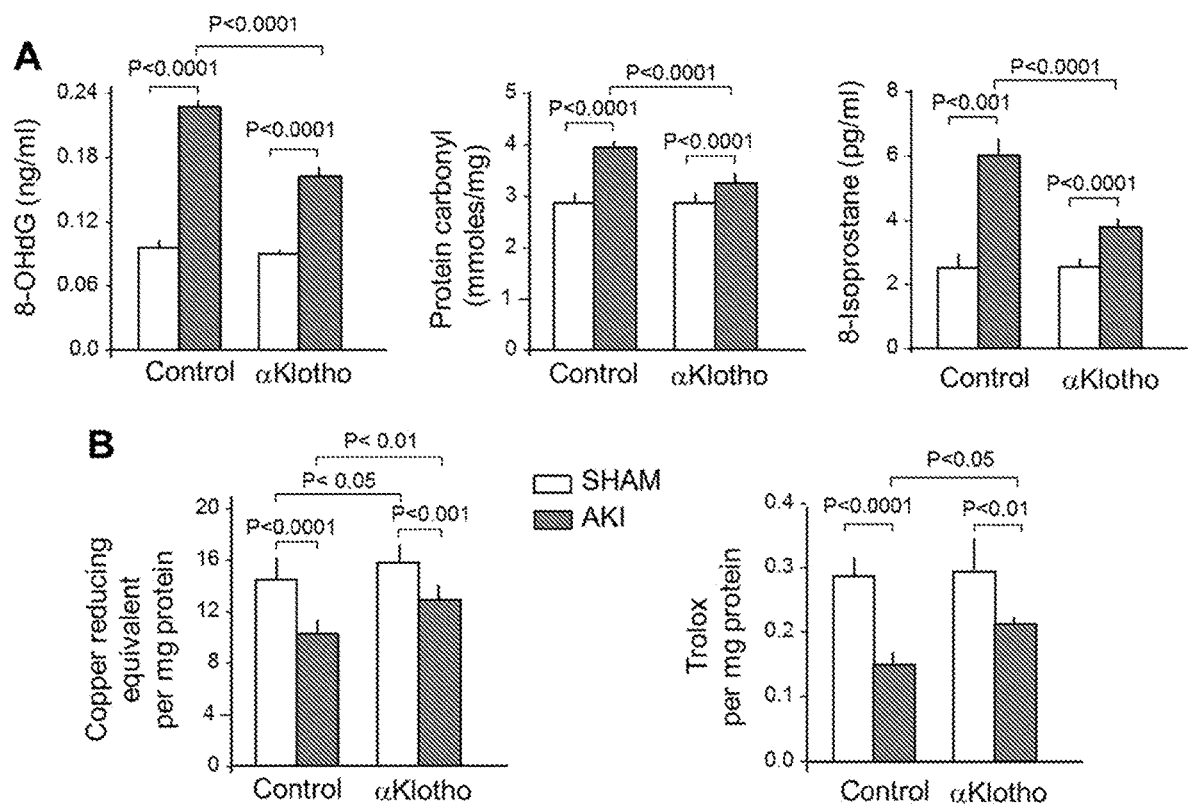
FIGS. 10A-B

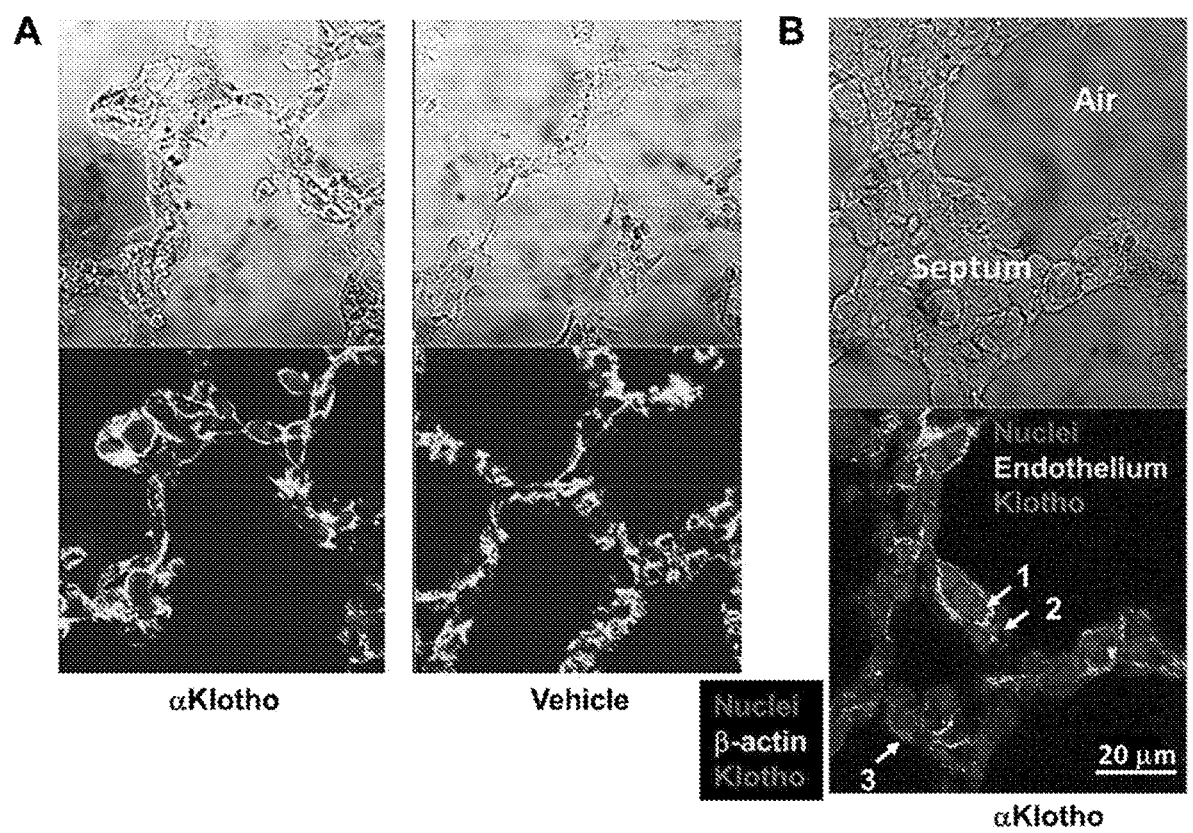
FIGS. 11A-B

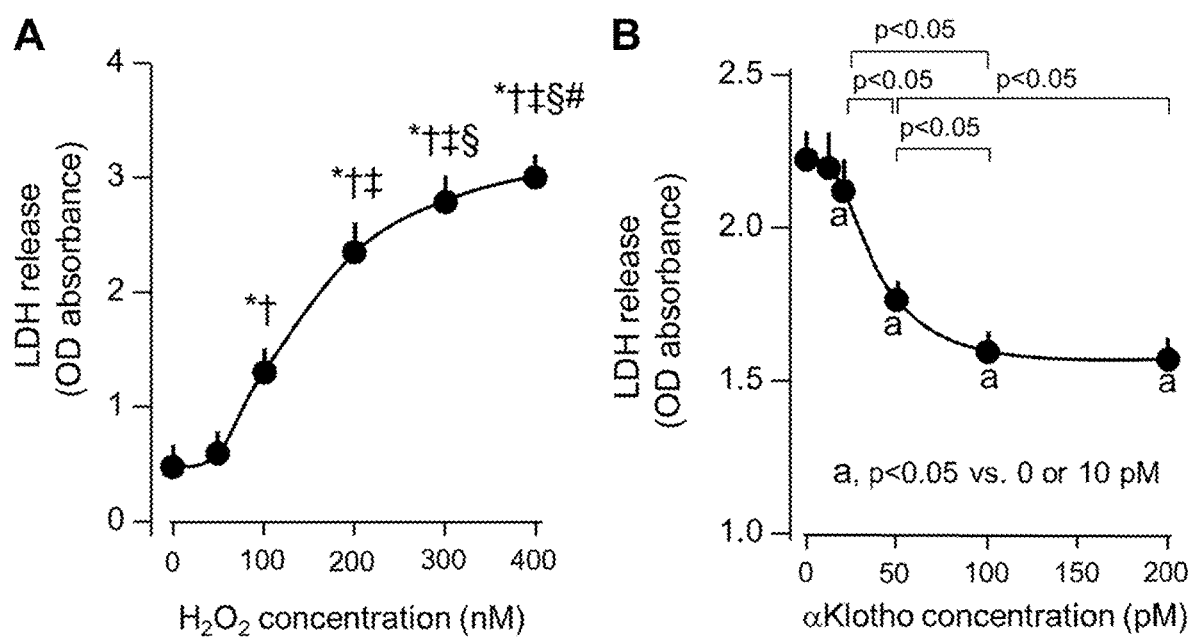
FIGS. 12A-B

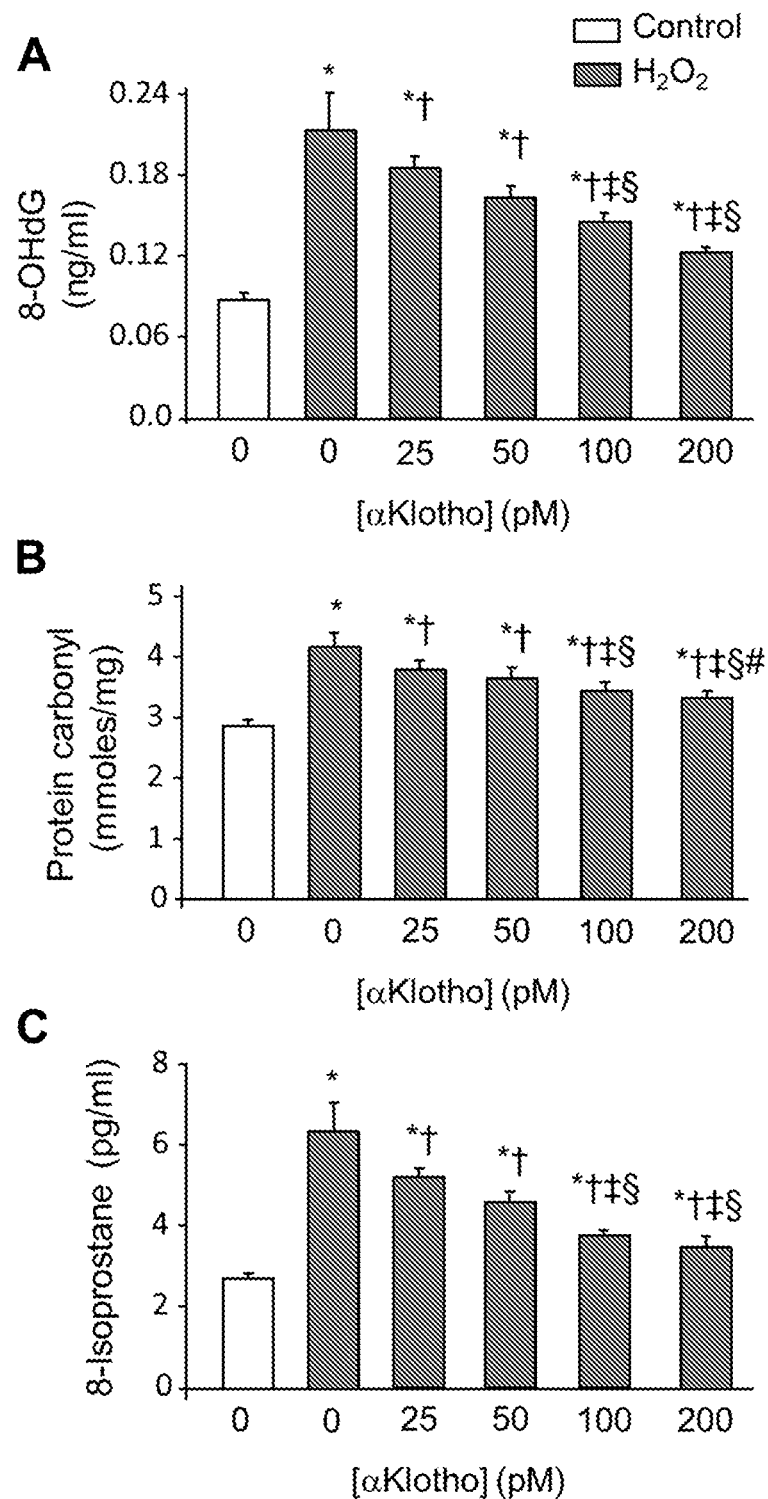
FIGS. 13A-C

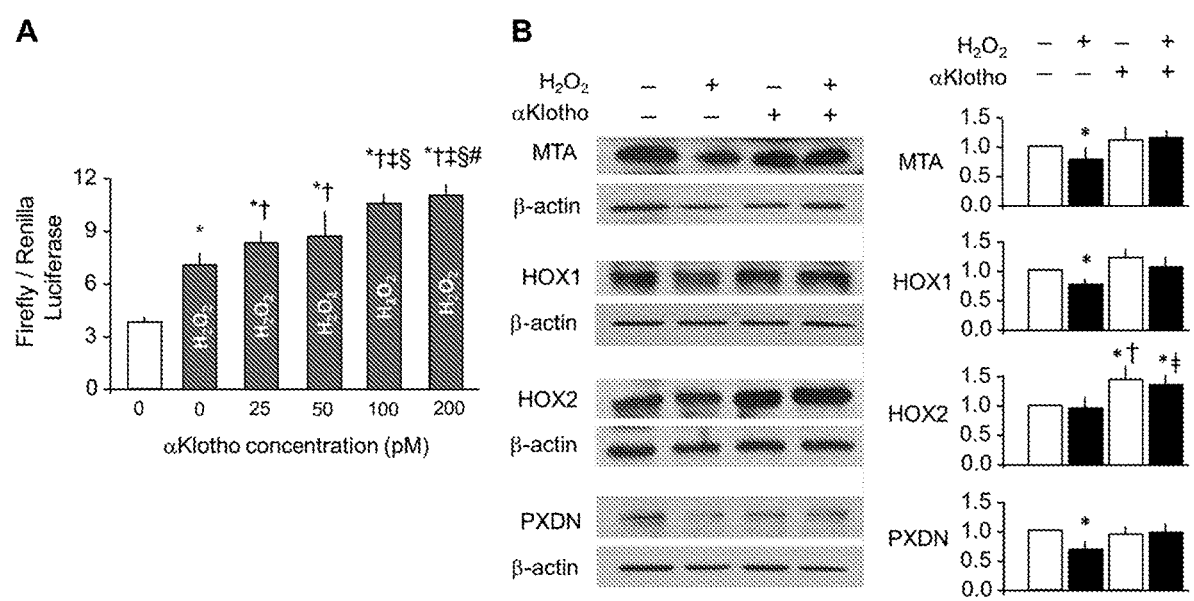
FIGS. 14A-B

NANOPARTICLES CONTAINING EXTRACELLULAR MATRIX FOR DRUG DELIVERY

This application is a national phase application under 35 U.S.C. § 371 of International Application No. PCT/US2016/041516, filed Jul. 8, 2016, which claims the benefit of U.S. Provisional Patent Application No. 62/190,591, filed Jul. 9, 2015, the entirety of each of which is incorporated herein by reference.

This invention was made with government support under grant numbers HL111146, DK901392, DK092461, and DK079328 awarded by The National Institutes of Health. The government has certain rights in the invention.

BACKGROUND

1. Field

The present disclosure relates generally to the field of pharmaceutics and medicine. More particularly, it concerns nanoparticle compositions for drug delivery, and uses thereof.

2. Description of Related Art

Lung diseases including chronic obstructive pulmonary disease, asthma, infections, as well as acute and chronic lung injury leading to fibrosis, constitute the third leading cause of death world-wide (Murray et al., 1997; Rabe et al., 2007; Tsushima et al., 2009). Inhalational drug delivery is a well-established route for targeted delivery of therapeutic agents (small molecules, proteins, and DNA) to the distal lung, and is commonly employed in clinical as well as experimental settings (Azarmi et al., 2008; Ku et al., 2008; Sung et al., 2007). Inhalational delivery takes advantage of the vast alveolar epithelial surface area to allow noninvasive delivery and rapid absorption of a large quantity of drug. Drug particles less than 5 µm in diameter have a high probability of deposition in the lung (Rees et al., 1982) while particles less than 2 µm in diameter tend to concentrate in the alveoli (Zanen et al., 1996; Zanen et al., 1994). Nanoparticles have been used as carrier to deliver therapeutic reagents to the lung. Nanoparticles have the potential to target specific lung cells in the treatment of respiratory disease (Azarmi et al., 2008). Incorporating drugs into nanoparticles provides additional benefits of increased drug concentration and sustained drug release, reducing the overall treatment dose and frequency, thereby decreasing local as well as systemic side effects (Sung et al., 2007).

Nonetheless, maximizing the deposition of therapeutic agents at the alveolar air-tissue interface and the uptake by alveolar epithelial cells remains challenging and problematic. This is at least in part due to the cyclic nature of ventilation that reduces the time for particle deposition, the efficient airway muco-ciliary clearance system, the alveolar fluid lining layer that can carry the delivered particles away from the epithelial cell surface, and the abundance of alveolar macrophages that detect and phagocytose particles, especially those greater than about 200 nm in diameter. It has been estimated that only about 20-30% of an inhaled bolus actually reaches the lung and undergoes uptake by lung cells. Thus, there is a need for compositions and methods for improved drug delivery to and cellular uptake by the lungs. Clearly, there is a need for improved compositions and methods for inhalational drug delivery.

SUMMARY

The present disclosure, in some aspects, overcomes limitations in the prior art by providing new and improved nanoparticles that can be used to deliver a drug or therapeutic to a mammalian subject (e.g., a human subject). The present disclosure is based, in part, on the discovery that nanoparticles that are coated in or contain decellularized extracellular matrix (ECM) on the surface of the nanoparticles exhibit surprising and unexpected improvements in the pharmacokinetics of the nanoparticles. For example, when nanoparticles (e.g., poly-lactic-(co)glycolic acid, PLGA, nanoparticles) coated with ECM were delivered in an aerosol or via inhalation, significant improvements in nanoparticle uptake into the lung and retention in the lung were observed. In some embodiments, lung-specific ECM may be obtained using decellularized lung tissue.

Rapid uptake of drug-loaded nanoparticles (NPs) is critical for effective delivery of therapeutic agents. As shown in the below examples, nanoparticles coated with ECM were observed to enhance NP uptake and retention by lung cells. In these experiments, fresh adult porcine lung tissue was decellularized and enzymatically digested into a soluble solution. The double emulsion method was utilized to fabricate core-shell poly(lactic-co-glycolic) (PLGA) nanoparticles loaded with bovine serum albumin (BSA) for protein release studies, 6-coumarin for cellular uptake studies, or human erythropoietin receptor (hEPOR) cDNA co-expressing green fluorescent protein (GFP) for in vivo gene expression studies. The ECM was coated onto nanoparticle surface by physical adsorption. No significant differences in the diameter, blood compatibility or cyto-compatibility were observed between coated and uncoated NPs. As compared to collagen-coated or uncoated nanoparticles, ECM-coated nanoparticles were observed to exhibit (i) higher cellular uptake by and (ii) delayed payload release in human lung epithelial cells. ECM-coated nanoparticles loaded with hEPOR-GFP cDNA were aerosolized and delivered into rat lung. Following single inhalation using uncoated nanoparticles, GFP expression in lung tissue progressively increased for up to 21 days. Using ECM-coated nanoparticles, GFP expression peaked by 10 to 14 days, then declined thereafter. These results demonstrate that coating NPs with lung-derived ECM enhances NP uptake by lung cells, delays release and expression of encapsulated DNA, and shortens the duration of peak gene expression.

In one aspect, the present disclosure relates to a pharmaceutical composition comprising a plurality of nanoparticles, wherein an exterior surface of the nanoparticles comprises or is at least partially coated with a decellularized extracellular matrix (ECM). The pharmaceutical composition may be formulated for inhalation or aerosol delivery. In some embodiments, the extracellular matrix comprises or consists of decellularized lung tissue. In some embodiments, the decellularized lung tissue is decellularized porcine lung tissue. The nanoparticles may comprise poly(lactic-co-glycolic) (PLGA), poly(lactic acid) (PLA), poly(glycolic acid) (PGA), gelatin, chitosan, liposome, or a combination thereof. In some embodiments, the nanoparticles are PLGA nanoparticles. In some embodiments, the nanoparticles are coated with the extracellular matrix. The nanoparticles may be generated via a single or double emulsion method. In some embodiments, the extracellular matrix is coated on the nanoparticles layer by layer or via physical adsorption. In some embodiments, said nanoparticles comprise a drug. In some embodiments, the pharmaceutical composition is formulated for inhalation or aerosol delivery. The drug may be a protein, a small molecule therapeutic, or a nucleic acid. In some embodiments, the drug is an anti-inflammatory agent, an antibiotic, or a chemotherapeutic. In some embodiments, the drug is an alpha-Klotho (αKlotho) protein or a nucleic acid encoding αKlotho. In some embodiments, the drug is EPO receptor protein or a nucleic acid encoding EPO receptor. In some embodiments, the drug is a cDNA encoding EPO receptor or human EPO receptor. As shown in Ravikumar et al. (2016b), inhalational delivery of nanoparticles containing cDNA encoding erythropoietin receptor (EpoR) may be used to effectively protect against a lung injury, such as hyperoxic lung injury. The pharmaceutical composition may further comprise an excipient.

Another aspect of the present disclosure relates to a method of treating a lung disease in a mammalian subject comprising administering a pharmaceutical preparation of the present disclosure or as described herein to the subject via inhalation or aerosol delivery, wherein the nanoparticles contain a drug. The subject may be a human. The disease may be a direct or indirect lung injury, an acute respiratory distress syndrome, a cancer, an infection, an inflammatory disease, a lung inflammatory disease, asthma, chronic obstructive pulmonary disorder, or an inflammatory disease of the lung parenchyma such as, e.g., an interstitial, or vascular lung disease. In some embodiments, the disease is a lung injury and the drug is an αKlotho protein or a DNA encoding αKlotho. The lung disease may be an acute lung injury, a hyperoxic lung injury, or an oxidative stress lung injury. In some embodiments, the disease is an acute respiratory distress syndrome or results either directly from an injury to the lung, or as a complication secondary to injury to another organ (e.g., in response to an acute kidney injury, acute heart failure, brain trauma, or extensive burns).

Yet another aspect of the present disclosure relates to a method of delivering a drug to a subject, comprising administering a pharmaceutical preparation of the present disclosure or as described herein to the subject, wherein the nanoparticles contain a drug. The subject may be a human. The pharmaceutical composition may be formulated for inhalation, aerosols, lung delivery, nasal delivery, airway instillation, oral administration, mucosal application, or vascular injection into a vein or artery.

Another aspect of the present disclosure relates to a method of treating lung injury in a mammalian subject comprising administering a pharmacologically effective or therapeutically effective amount of an αKlotho protein or a DNA encoding αKlotho to the subject. In some embodiments, the lung injury is an acute lung injury (ALI) or acute respiratory distress syndrome. The subject may be a human. In some embodiments, the lung injury results from an injury to the lung. In some embodiments, the lung injury results from a complication secondary to injury to another organ (e.g., acute kidney injury, acute heart failure, brain trauma, or extensive burns). In some embodiments, the αKlotho protein or the DNA encoding αKlotho is administered via inhalation or aerosol delivery, nasal, or airway instillation, oral administration, mucosal application, or injection into a vein or artery. In some embodiments, the αKlotho protein or the DNA encoding αKlotho is comprised in a pharmaceutical preparation, wherein the pharmaceutical preparation comprises an excipient. In some embodiments, the αKlotho protein or the DNA encoding αKlotho is comprised in a nanoparticle. In some embodiments, an exterior surface of the nanoparticle comprises or is at least partially or coated with a decellularized extracellular matrix (ECM).

Acute lung injury (ALI) is a common and serious condition that can result from direct insult to the lung such as physical trauma or exposure to heat, fumes, toxic chemicals, infection or inflammatory agents. ALI can also develop as a life-threatening complication of systemic organ failure due to sepsis, extensive burns, acute kidney injury (AKI), heart failure or brain trauma, that secondarily cause fluid leakage and inflammation in the lung leading to respiratory failure. Patients suffering from ALI often require mechanical ventilation and exposure to a high oxygen concentration, which can cause trauma and oxygen toxicity to the lung to further aggravate existing lung injury and escalate morbidity and mortality. Survivors of ALI often endure long-term disability such as lung fibrosis and chronic respiratory failure. Conventional treatment of ALI remains largely supportive except for the use of antibiotics in infections and lung transplantation in end-stage respiratory failure; the latter is limited by donor shortage and complications related to graft rejection and immunosuppression. Regardless of the cause of ALI, current therapeutic regimens cannot reduce in-hospital mortality below 40%. (Rubenfeld et al., 2005). There is a dire need for innovative methods to not only reduce lung injury but also actively promote repair and re-growth of normal lung tissue.

Alpha-Klotho (αKlotho) was discovered when disruption of its gene led to accelerated organ degeneration, premature ageing and early death (Kuro-o et al., 1997). αKlotho is a circulating cytoprotective protein that originates predominantly from the kidney and secreted into blood, urine, and cerebrospinal fluid (Hu et al., 2012; Imura et al., 2004; Matsumura et al., 1998). Secreted αKlotho exerts multiple tissue protective effects such as anti-oxidation and anti-fibrosis (Hu et al., 2013a; Hu et al., 2013b) on distant organs including the lung. Acute kidney injury (AKI) is associated with a state of severe αKlotho deficiency and the lung is particularly vulnerable to αKlotho deficiency. In the below examples, αKlotho deficiency was observed to contribute to the ALI that develops in AKI. In a rodent model of AKI, the inventors observed alveolar interstitial edema and increased oxidative damage to DNA, protein and lipids in lung tissue. Administration of recombinant αKlotho post-AKI to restore its serum level did not change the peak plasma creatinine level but reduced lung edema and oxidative damage and increased endogenous anti-oxidative capacity in the lung. To explore the direct action of αKlotho on lung cells, the inventors first showed that circulating αKlotho exits the pulmonary alveolar capillaries to access the septal interstitium. Oxidative stress was simulated with hydrogen peroxide in cultured alveolar epithelial cells, and it was observed that αKlotho directly protects the cells with detectable effect at 20 pM and half maximal effect at 40-50 pM, which is compatible with the normal circulating levels of αKlotho. αKlotho addition activated an antioxidant response element (ARE) reporter and increased the transcripts of Nrf2 (nuclear-factor-E2-related factor)-2 regulated target genes. Without wishing to be bound by any theory, these results support the idea that αKlotho deficiency in AKI contributes to ALI by decreasing the endogenous antioxidative capacity of lung. In some aspects, αKlotho protein or DNA may be used to mitigate pulmonary complications in AKI (Suga et al., 2000; Ravikikumar et al., 2016a; Doi et al., 2011; Faubel et al., 2008).

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 2B) Transmission electron microscope (TEM) image of uncoated and coated PLGA NPs. (FIG. 2C-D) Stability studies of uncoated and coated PLGA NPs in phosphate-buffered saline (PBS) (FIG. 2D) and culture media with 10% serum at 37° C. (FIG. 2D).

FIGS. 3A-E: Hemocompatibility studies blood clotting formation and hemolysis of uncoated and ECM-coated PLGA NPs (FIGS. 3A-C). Digital camera recording of clot formation in human whole blood alone (FIG. 3A), or whole blood added to uncoated PLGA NPs (FIG. 3B) or ECM-coated PLGA NPs (FIG. 3C) after 10, 20, 30 and 60 minutes (left to right tubes). (FIG. 3D) Absorbance measurement at 540 nm of the lysate of human blood after exposed to the blood at each time point. (FIG. 3E) Hemolysis rate of uncoated and coated PLGA NPs compared with positive control (saline and de-ionized water).

FIGS. 6A-B: Optimization of coating technique using adsorption or layer-by-layer (LBL) technique showing (FIG. 6A) hydrodynamic size and (FIG. 6B) cellular nanoparticle uptake by AEC1s by feeding NPs coated using different concentrations of ECM and coating methods. Uncoated PLGA NP was a control. Mean±SD. *p<0.05, compared with uncoated NP.

FIGS. 7A-B: (FIG. 7A) In vitro cellular uptake of uncoated, collagen-coated and ECM-coated PLGA NPs (by the adsorption method) by human type I alveolar epithelial cells (AEC1 s) using fluorescence intensity and bicinchoninic acid (BCA) assay measurement. Mean±SD. *p<0.05, compared with uncoated or collagen coated NP. (FIG. 7B) Images of A549 human alveolar epithelial cells that have taken up the nanoparticles containing fluorescent labels, visualized under differential interference contrast (DIC, left), fluorescent microscopy (middle), and superimposed DIC+fluorescent microcopy (right). Bar=10 μm.

FIGS. 8A-C: Fluorescent protein expression is shown in rat lungs 4, 8, 14 and 21 days following inhalation of nebulized ECM-coated or uncoated PLGA NPs containing hEPOR cDNA co-expressing GFP. (FIG. 8A) Tissue fluorescence was detected by a bioimager in serial lung slices and (FIG. 8B) the average radiant efficiency was quantified. Mean±SD. P<0.05: † vs. control (inhalation without NPs), ‡ vs. uncoated NPs. (FIG. 8C) Tissue fluorescence was also demonstrated by light microscopy. Bar=50 μm.

FIGS. 9A-D: αKlotho deficiency and repletion in acute kidney injury (AKI). Sprague-Dawley rats underwent bilateral ischemia-reperfusion injury (IRI), and lungs were harvested 3 days later. The control group underwent general anesthesia and laparotomy with manual manipulation of the kidneys but without IRI (Sham). Rats received intraperitoneal injection of either αKlotho-containing or control conditioned media 6 h after surgery. (FIG. 9A) Severity of AKI was measured by serum creatinine level in the animals 3 days after IRI. (FIG. 9B) Serum αKlotho level was measured by immunoprecipitation-immunoblot 3 days after IRI at the time of lung harvest. Representative blots are shown. IgG-HC, immunoglobulin heavy chain. (FIG. 9C) Representative lung histology (Trichrome stain). (FIG. 9D) $Na^+$ to dry lung weight ratio as a measure of interstitial edema. Means±SD (n=7 to 8 animals per group). Statistical significance was assessed by ANOVA.

FIGS. 10A-B: Acute lung injury in acute kidney injury (AKI). Sprague-Dawley rats underwent bilateral ischemia-reperfusion injury (IRI) and lungs were harvested 3 days later. The control group underwent general anesthesia and laparotomy with manual manipulation of the kidneys but without IRI (Sham). Rats received intraperitoneal injection with either αKlotho-containing or control conditioned media 6 hours after surgery and lungs were harvested 3 days later. (FIG. 10A) Markers of DNA (8-hydroxy-2'-deoxyguanosine; 8OHdG) protein (protein carbonyl), and lipid (8-isoprosane) oxidative damage. (FIG. 10B) Markers for endogenous anti-oxidative capacity were assessed by a copper-based (left) or an iron-based (Trolox, right) assay; n=7 to 8 animals per group. Bars and error bars are mean±SD. Statistical significance was assessed by ANOVA. The p values are shown in the figure.

FIGS. 11A-B: (FIG. 11A) 20 min after injection with FLAG-αKlotho or vehicle. Representative images of FLAG-αKlotho (anti-FLAG with Alexa fluor 555-coupled secondary antibody; red), β-actin (Oregon Green 488-coupled phalloidin; green), and nuclei (SYTO 61; red digitally converted to blue) are shown. (FIG. 11B) 30 mins after injection with FLAG-αKlotho. Representative images of FLAG-αKlotho (anti-FLAG with Alexa fluor 555-coupled secondary antibody; red), endothelium (anti-CD31 with Alexa fluor 488-coupled secondary antibody; green), and nuclei (SYTO 61; red digitally converted to blue) are shown.

Figure 1:
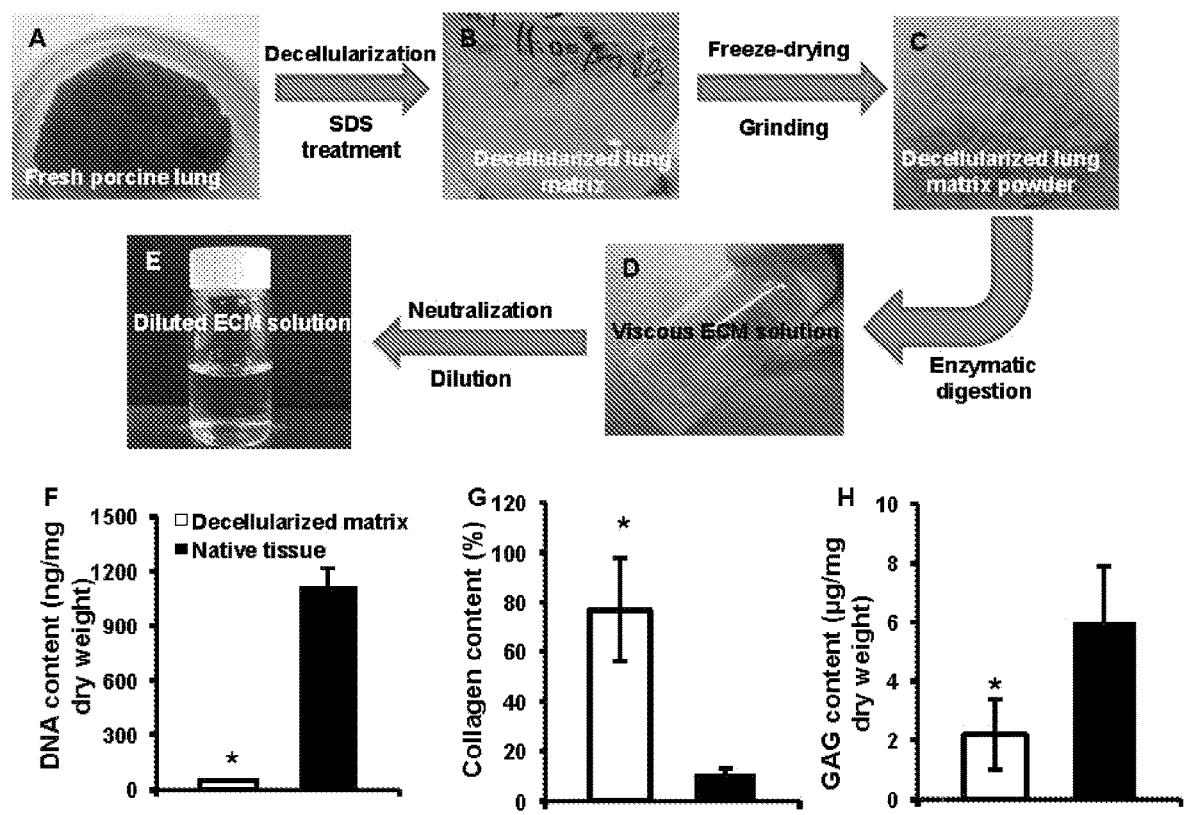
FIGS. 1A-H: Illustration of the decellurization process (FIGS. 1A-E) and characterization (content of DNA, collagen, and glycoaminoglycans, FIGS. 1F-H, respectively) of the decellularized ECM.

Arrows indicate localization of FLAG-αKlotho: 1. Intracapillary; 2—interstitium; 3—epithelium, possibly an alveolar type 2 cell.

FIGS. 12A-B: Cytoprotection by αKlotho in an in vitro hydrogen peroxide ($H_2O_2$) model of oxidative damage. (FIG. 12A) Dose-response of $H_2O_2$ on lactate dehydrogenase (LDH) release as a marker of cell death. A549 lung epithelial cells were incubated with the indicated $H_2O_2$ dose for 4 hours. *$p<0.0001$ vs. 0 nmol/l $H_2O_2$; † $p<0.0001$ vs. 50 nmol/l $H_2O_2$; ‡ $p<0.001$ vs. 100 nmol/l $H_2O_2$; § $p<0.05$ vs. 200 nmol/l $H_2O_2$; # $p<0.05$ vs. 300 nmol/l $H_2O_2$. (FIG. 12B) Dose response of purified recombinant αKlotho on $H_2O_2$ induced A549 cell death. P values are indicated. a, $p<0.05$ vs. 0 or 10 pM αKlotho concentration. Average of 3 independent experiments (mean±SD). Statistical significance was assessed by ANOVA. The p values are shown in the figure.

FIGS. 13A-C: Markers of oxidative damage in cultured lung epithelial cells and protection by αKlotho protein. A549 cells were treated with 200 nM $H_2O_2$ for 3 hr with different concentrations of recombinant αKlotho. (FIG. 13A) DNA (8-hydroxy-2'-deoxyguanosine; 8-OHdG), (FIG. 13B) Protein (protein carbonyl), and (FIG. 13C) lipid (8-isoprostane) oxidative damage. Average of 3 independent experiments (mean±SD). Statistical significance was evaluated by ANOVA. *$p<0.0001$ vs. untreated cells; ‡ $p<0.0001$ vs. cells treated with 200 nmol/l $H_2O_2$ and 0 pM αKlotho; ‡ $p<0.001$ vs. cells treated with 200 nmol/l $H_2O_2$ and 25 pM αKlotho; § $p<0.05$ vs. cells treated with 200 nmol/l $H_2O_2$ and 50 pM αKlotho; # $p<0.0001$ vs. cells treated with 200 nmol/l $H_2O_2$ and 100 pM αKlotho.

FIGS. 14A-B: Activation of Nrf2 antioxidative pathway in lung epithelial cells by αKlotho. (FIG. 14A) A549 cells were transfected with an ARE (antioxidant responsive element)-luciferase reporter and were treated with the stated concentration of recombinant αKlotho. Activation of ARE is expressed as firefly luciferase luminescence ratio to the control *Renilla*. Average of 3 independent experiments. Mean±SD. Statistical significance was assessed by ANOVA. *$p<0.0001$ vs. untreated cells; † $p<0.001$ vs. cells treated with 200 nM $H_2O_2$ and 0 pM αKlotho; ‡ $p<0.0001$ vs. cells treated with 200 nmol/l $H_2O_2$ and 25 pM αKlotho; § $p<0.0001$ vs. cells treated with 200 nM $H_2O_2$ and 50 pM αKlotho; # $p<0.05$ vs. cells treated with 200 nM $H_2O_2$ and 100 pM αKlotho (FIG. 14B) Left: Selected anti-oxidant protein expression were quantified by immunoblot. MTA: methalothionine, HOX1 and 2: heme oxygenase 1 and 2, PXDN: peroxidasin. β-actin served as loading control. Right: Densitometry of antioxidant levels was normalized to β-actin and expressed as a ratio to control (no $H_2O_2$, no αKlotho). Average of 3 independent experiments. Mean±SD. Statistical significance was assessed by ANOVA. *$p<0.05$ vs. control. † $p<0.05$ vs. 200 mM $H_2O_2$ and no αKlotho. ⁺ $p=0.065$ compared to 200 mM $H_2O_2$ and no αKlotho.

DESCRIPTION OF ILLUSTRATIVE EMBODIMENTS

The present disclosure overcomes limitations in the prior art by providing improved nanoparticles that may be used, e.g., for improved drug delivery to the lungs of a subject. The present disclosure is based, in some aspects, on the finding that nanoparticles (e.g., PLGA nanoparticles) that are coated with or comprise ECM exhibit improved pharmacokinetics

II. EXTRACELLULAR MATRIX (ECM)

A variety of methods may be used to prepare extracellular matrix (ECM). Generally, ECM refers to decellularized tissue, preferably from a mammal such as a pig. The tissue may be lung, small intestinal submucosa (SIS), or from other organs. In some embodiments, the decellularized ECM is obtained from lung tissue from a pig. In some embodiments, the decellularized ECM is obtained from porcine lung. As used herein "ECM" preferably refers to decellularized ECM.

In some embodiments, ECM is prepared as follows. Fresh tissue (e.g., lung tissue) may be isolated from adult a mammal (e.g., a pig) and processed into an ECM solution through decellularization and enzymatic digestion using sodium dodecyl sulfate (SDS). Typically, the resulting ECM may thus induce little or no immune response in a subject, and various methods (e.g., DNA residue quantification) may be used to verify the quality of the ECM generated. Decellularized ECM typically contains two major components, collagen and glycosamingoglycan, along with a mixture of proteins, peptides and growth factors. The collagen content may be higher, while the GAG content may be lower, as compared to native tissue. After enzymatic digestion with enzymes, e.g., pepsin, a flowable ECM solution may be obtained. The enzyme treatment can cleave or reduce high molecular weight proteins and may also de-assemble the crosslinking structure, making the ECM more soluble in PBS.

In some embodiments decellularized ECM may be coated onto nanoparticles (e.g., PLGA nanoparticles) using adsorption. For example, a diluted solution of decellularized ECM was used for coating onto nanoparticles by adsorption. A variety of methods may be used for the decellularization and solublization process used to isolate tissue-derived ECM such as heart (Seif-Naraghi et al., 2013), skin (Wolf M T, et al., 2012.), brain and spin cord (Medberry et al., 2013), meniscus (Wu et al., 2015) and bone (Sawkins et al., 2013). Generally, the method used may try to preserve biological components, especially the water-soluble bioactive molecules while completely removing cellular components that might cause an immunogenic response. In some embodiments, the process is conducted in water, and the ECM may be washed repeatedly to remove SDS residue. The ECM may contain a variety of additional proteins (Sokocevic et al., 2013).

III. NANOPARTICLES

In some aspects, nanoparticles comprising or coated with ECM are provided that may be used for inhalation or aerosol delivery. In some embodiments, the nanoparticles comprise poly(lactic-co-glycolic acid) (PLGA). PLGA nanoparticles (NPs) may be fabricated, e.g., using a modified double emulsion technique as described, e.g., in (Menon et al., 2012). Additional methods that may be used to generate PLGA-containing nanoparticles include those described in, e.g., (Danhier et al., 2012) and (Menon et al., 2014). In some embodiments the nanoparticles are PLGA nanoparticles. In some embodiments, the nanoparticles are surface-modified or bioconjugated, e.g., to improve targeting capability and delivery of an encapsulated drug.

In some embodiments, the nanoparticles may comprise poly(lactic acid) (PLA), poly(glycolic acid) (PGA), and/or PLGA. In some embodiments, the nanoparticle may contain natural polymers such as gelatin and chitosan. In some embodiments, the nanoparticle may contain one or more additional agent such as, e.g., a neutral lipid, a neutral phospholipid, a charged lipid, and/or a charged phospholipid. For example, the neutral phospholipid may be a phosphatidylcholine, such as DOPC, egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, or dilinoleoylphosphatidylcholine. In certain embodiments the neutral phospholipid is a phosphatidylethanolamine, such as dioleoylphosphatidylethanolamine ("DOPE"), distearoylphophatidylethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), or lysophosphatidylethanolamine. The charged phospholipid may be positively or negatively charged. The negatively charged phospholipid may be, e.g., a phosphatidylserine (e.g., dimyristoyl phosphatidylserine ("DMPS"), dipalmitoyl phosphatidylserine ("DPPS"), or brain phosphatidylserine ("BPS")) or a phosphatidylglycerol (e.g., dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), or dioleoylphosphatidylglycerol ("DOPG")). In some embodiments, the nanoparticles may further comprise chitosan, gelatin, alginate, cholesterol, PEI (polyethyleneimine), and/or polyethyleneglycol (PEG), for example in combination with PLGA. The phospholipid may be a naturally-occurring phospholipid or a synthetic phospholipid. One or more additional surface modification may be included in the nanoparticles, e.g., as described in Enayati et al., 2012; Fields et al., 2012; Ahmed et al., 2012; or Fontana et al., 2001.

The size of the nanoparticles may be varied, as desired. In some embodiments, the nanoparticles are about 10-1000 nm, with a more preferred range of about 50-250 nm in diameter.

In some embodiments, the following method is used to generate PLGA nanoparticles. The emulsion-solvent evaporation method may be used to prepare PLGA nanoparticles. For this procedure, 3% w/v PLGA solution may be prepared in chloroform. The solution may then be added to an aqueous solution of 5% w/v PVA to create an emulsion, and then sonicated. This particle suspension may be stirred (e.g., overnight at room temperature), to allow the solvent to evaporate. Nanoparticles may be recovered by ultracentrifugation at 25,000 rpm for 30 min at 10° C. For drug-loaded nanoparticles, a solution containing the drug (e.g., a therapeutic peptide, protein, small molecule, DNA, cDNA, RNA, RNAi) in water may be emulsified in PLGA solution. If it is desired to include chitosan (or other ingredient) in the nanoparticles, carboxymethyl chitosan (or other ingredient) may be mixed with PVA solution and allowed to be adsorbed onto the surface of the PLGA nanoparticles. If it is desired the nanoparticles may be lyophilized and stored in powder form (e.g., at −20° C.) when not being used. In some embodiments, nanoparticles may be constituted in either DI water, media or saline prior to use.

IV. DRUGS

In some embodiments, the nanoparticles may contain a drug such as, e.g., a small molecule, a nucleic acid (e.g., a DNA or RNA), or a protein. The protein may be a peptide or a polypeptide. In some embodiments, the nucleic acid encodes a therapeutic protein. The nucleic acid may include a promoter that is operably linked to a sequence for the expression of a therapeutic protein. In some embodiments, the nucleic acid may encode a small inhibitory RNA (siRNA or RNAi), a micro RNA (miRNA), an antisense, a gene therapy, or a therapeutic protein.

In some embodiments, the drug may be an anti-inflammatory drug, a chemotherapeutic, a tissue protective or a growth promoting substance. For example, in some embodiments the drug may be a therapeutic to treat asthma, chronic obstructive pulmonary disorder (COPD), cancer (e.g., a lung cancer), acute lung injury (ALI), or chronic lung fibrosis.

In some embodiments, the drug is used to treat a lung injury such as an acute lung injury. For example, in some embodiments, a protein or nucleic acid encoding αKlotho, EPO receptor (e.g., human EPO receptor), or other molecules may be included in the nanoparticles. For example, αKlotho is described in (Hu et al., 2013; Ravikumar et al., 2016a), and αKlotho may have the sequence of Genbank accession number: NM_004795, Gene ID number: 9365.

αKlotho is a single-pass transmembrane protein that functions as an obligate co-receptor for FGF23 and is crucial for mineral metabolism (Hu et al., 2013). The extracellular domain of αKlotho is released via cleavage by secretases into blood, urine, and cerebrospinal fluid as endocrine soluble αKlotho (Hu et al., 2012; Imura et al., 2004) exerting multiple effects, including anti-oxidation and anti-fibrosis, on distant organs (Hu et al., 2013a; Hu et al., 2013b). αKlotho is not normally expressed in the lung, but the lung is highly sensitive to αKlotho-mediated protection, and the alveolar capillary bed is constantly exposed to circulating αKlotho via perfusion by the entire cardiac output. Hemizygous genetic αKlotho haplo-insufficient mice are normal in all organs at baseline except the lung, which exhibits age-exacerbated degenerative changes such as air space enlargement and increased compliance (Suga et al., 2000; Ravikumar et al., 2014). Administered exogenous αKlotho may protect the lung and lung cells against acute oxidative damage by increasing endogenous anti-oxidative capacity in vivo and in vitro (Ravikumar et al., 2014).

Acute kidney injury (AKI) has been associated with a state of transient severe systemic αKlotho deficiency in rodents and humans (Hu et al., 2010; Panesso et al., 2014). AKI per se is also a state of heightened oxidative stress (Nath and Norby, 2000). As shown in the below examples, the inventors have investigated the possibility that αKlotho deficiency in AKI contributes to acute lung injury (ALI). Without wishing to be bound by any theory, the data presented in the below examples supports the idea that αKlotho deficiency may function as a mediator of pulmonary dysfunction in AKI. A rodent renal ischemia-reperfusion model of AKI was used to characterize αKlotho deficiency and quantify ALI, and it was observed that αKlotho repletion improves ALI in AKI.

V. PHARMACEUTICAL PREPARATIONS

In some embodiments, the nanoparticles are administered to a mammalian subject (e.g., a human) by inhalation or via an aerosol pharmaceutical composition. Nonetheless, in various embodiments, the pharmaceutical composition may be formulated for parenteral, intravenous, intradermal, intrathecal, intraarterial, intraperitoneal, intranasal, intravaginal, intrarectal, intra-ocular, intramuscular, subcutaneous, mucosal, oral, topical, intra-airway or inhalational administration.

Nanoparticle compositions as described herein, optionally containing a drug or therapeutic agent, may be dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one nanoparticle (e.g., containing a drug or therapeutic agent) or additional active ingredient will be known to those of skill in the art in light of the present disclosure, as exemplified by *Remington: The Science and Practice of Pharmacy, 21$^{st}$ Ed.*, Lippincott Williams and Wilkins, 2005, incorporated herein by reference. Moreover, for animal (e.g., human) administration, it will be understood that preparations should typically meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

Nanoparticles described herein may comprise different types of carriers depending on whether it is to be administered in solid, liquid or aerosol form, and whether it need to be sterile for such routes of administration as injection. The present disclosure can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, *Remington: The Science and Practice of Pharmacy, 21$^{st}$ Ed.*, Lippincott Williams and Wilkins, 2005).

A drug or active ingredient in a nanoparticle may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

In some embodiments, the nanoparticles or a pharmaceutical composition comprising nanoparticles as described herein may be delivered by eye drops, intranasal sprays, inhalation, and/or other aerosol delivery vehicles. Methods for delivering compositions directly to the lungs via nasal aerosol sprays has been described, e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term "aerosol" refers to a colloidal system of finely divided solid of liquid particles dispersed in a liquefied or pressurized gas propellant. The typical aerosol of the present disclosure for inhalation may contain a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Extracellular Matrix Coating Enhances Nanoparticle Uptake and Delays Release by Lung Epithelial Cells Materials—Poly (lactic-co-glycolic acid) (PLGA, 50:50) was purchased from the Lakeshore Biomaterials (Birmingham, Ala.). Sodium dodecyl sulfate (SDS), dichloromethane, 6-coumarin, and polyvinyl alcohol (PVA, MW 31,000-50,000 and 87-89% hydrolyzed) were purchased from Sigma Aldrich (St. Louis, Mo.). Albumin from bovine serum (BSA) and Texas Red® conjugated BSA were purchased from Life technology (Carlsbad, Calif.). Type I alveolar epithelial cells (AEC1s) were purchased from Applied Biological Materials Inc. (Richmond, BC, Canada). All other chemicals were purchased from Sigma Aldrich (St. Louis, Mo.).

Preparation of porcine lung ECM solution (FIGS. 1A-E)—The porcine lung ECM solution was obtained by deceullarization and pepsin digestion, as follows. Briefly, the lungs were harvested from adult pigs (weighing 80-100 kg) from a local slaughterhouse, cut into slices (1 mm in thickness) and rinsed using deionized (DI) water. Then the lung slices were processed by decellularization in 1% (w/v) SDS solution under stirring for 3-4 days, until the lung matrix turned white. The SDS solution was refreshed every day. The decellularized matrix was rinsed using large amount of DI water overnight to remove SDS residual, and then freeze-dried for 3 day. The dry decellularized lung matrix further was solubilized at an ECM concentration of 15 mg/mL in 1 mg/mL pepsin/0.01 M HCl solution. After 3 days, the decellularized lung matrix was solubilized and filtered to achieve the desired final particle size and concentration. The solution was neutralized using 0.1 M NaOH and 10×PBS, and diluted to desirable ECM concentrations using 1×PBS for nanoparticle coating.

Fabrication of polymeric PLGA nanoparticles—PLGA nanoparticles (NPs) were fabricated using a modified double emulsion technique as previously described (Menon et al., 2012). Briefly, 400 µL of 1% w/v Texas-Red BSA solution was added drop wise into 3 mL of 1.33% w/v PLGA solution that was dissolved in dichloromethane and then sonicated at 20 W for 1 min. This first emulsion solution was then added drop wise to 12 mL of 5% polyvinyl alcohol (PVA) solution and sonicated at 40 W for 3 min. This double emulsion solution was de-solvated overnight with stirring at room temperature. PLGA NPs were washed and collected using ultracentrifugation at 15,000 rpm for 30 minutes and lyophilization. The supernatant were collected to determine the loading efficiency of Texas-Red BSA. For cellular uptake and cell compatibility assessments, 6-coumarin loaded and unloaded PLGA NPs were fabricated using double-emulsion techniques as previously described (Sung et al., 2007).

PLGA NPs coated with porcine ECM by adsorption technique—PLGA NPs coated with porcine ECM were fabricated using modified adsorption technique (Booth et al., 2002). 10 mg NPs were suspended in 10 ml DI water and then mixed with 40 ml of porcine ECM solution at predetermined concentrations. The mixed solution was rotated on a rotator for 24 h and then the nanoparticles were collected by ultracentrifugation at 15,000 rpm for 30 min. The collected NPs were freeze-dried for further use. As a positive control, PLGA NPs coated with rat tail collagen type I was fabricated by immersing uncoated PLGA NPs in a 0.01% w/v of collagen solution in 0.1 M acetic acid.

NP Characterization—Particle size, polydispersity and zeta potential were measured using dynamic light scattering (DLS; ZetaPALS DLS detector, Brookhaven Instruments, Holtsville, N.Y.). Nanoparticle solution were prepared at 1 mg/ml concentration, and added into the transparent cuvette with the fixed amount of de-ionized water for testing. The morphology of the nanoparticles was observed under a transmission electron microscope (TEM; Hitachi H-9500 High resolution Transmission Electron Microscope). Nanoparticle solution was dropped on an oxygen plasma treated and Formvar-coated 200-mesh copper grid (Electron Microscopy Sciences, Hartfield, Pa.). The water was removed using a filter paper and then 10 µL of 0.5% of vinyl acetate solution was dropped on the grid at room temperature. The sample was dried in the air overnight for imaging. In vitro stability of nanoparticles was evaluated using dynamic light scattering (DLS) in term of particle size with time. Nanoparticle solutions at 1 mg/ml were prepared using PBS or cell culture medium with 10% fetal bovine serum (FBS; Atlanta Biological, Lawerenceville, Ga.), and were added into transparent cuvette. The cuvette was incubated at 37° C. for 2 d, and then the particle size was measured every 12 h using DLS instrument. Four replicates were used for analysis.

Protein release kinetic profile—The stock solution of 1 mg/ml Texas-Red BSA-loaded PLGA NPs was added into a dialysis tubing (100 kDa molecular weight cut-off, Spectrum Laboratories Inc., Rancho Dominguez, Calif.), and then placed into PBS solution with pH 7.4 at 37° C. for 28 days. At pre-determined time points, 1 mL of dialysate was collected and kept in microcentrifuge tubes at −20° C. for future analysis, and 1 mL fresh PBS solution was replenished. The measurement of fluorescent intensity of Texas-Red BSA was performed on an ultraviolet-spectrophotometer (Infinite M-200, Tecan) at 480 nm (excitation) and 615 nm (emission). A Texas-Red BSA standard curve was recorded using series of BSA solutions with known concentrations to determine the concentration of released Texas-Red BSA. Four replicates were used.

Human blood clotting measurement—The protocol of human whole blood collection was approved by the Institutional Review Board (IRB) of the University of Texas at Arlington. Human whole blood was drawn into anti-coagulant tubes, which contain trisodium citrate, citric acid and dextrose. Nanoparticle solutions were prepared in 0.9% saline and then added into 1.5 mL microcentrifuge tubes. To prepare the human blood clotting solution, 0.85 mL of calcium chloride solution (0.1M) was added into 8.5 mL anti-coagulated blood, and then 50 µL of blood were added into the tube containing nanoparticle solution. Blood solutions served as a control. After a pre-determined time point (10, 20, 30, and 60 minutes), 1.5 mL-distilled water were added, and incubated at room temperature for 5 min to terminate the reaction. Then, 200 µL of the lysate were collected from each samples and added into 96-well plates. To determine the clotting cascade, the lysate were measured the absorbance at 540 nm using an ultraviolet-spectrometer (Infinite M-200, Tecan) (Lin et al., 2004). Eight replicates were used for analysis.

Hemolysis assessment—Nanoparticle solutions at various concentrations were prepared in 0.9% saline. To prepare a negative control and a positive control, 200 µL of anti-coagulated blood were diluted in 10 ml 0.9% saline solution and 10 mL DI water, respectively. 10 µL of nanoparticle solution was added into a microcentrifuge tube and then 200 µL of blood solution were added. Samples were placed in an orbital shaker and incubated at 37° C. for 2 h. The samples were then centrifuged at 1000 g for 10 min to obtain the supernatant. The supernatant was transferred into a 96-well plate and the absorbance at 545 nm was recorded under an ultraviolet-spectrometer (Liu et al., 2009). Eight replicates were used for analysis.

NP cytocompatibility—Human alveolar type I epithelial cells (AEC1s) were pre-seeded in collagen I cellware 96 well-plates (Corning, N.Y.) at a 5000 cells per well and incubated at 37° C. and 5% $CO_2$ for 24 h in Prigrow III medium with 10% fetal bovine serum (FBS) and 1% penicillin/streptomycin. The medium was then replaced with nanoparticle suspensions in medium at various concentrations (n=4). After 24 h incubation, the medium was removed and the samples were washed using PBS. The samples were treated with 3-(4,5-dimethylthiazol-2-yl)-5-(3-carboxymethoxyphenyl)-2-(4-sulfophenyl)-2H-tetrazolium (MTS) reagent (CellTiter 96® AQueous One Solution Cell Proliferation Assay, Promega, Madison, Wis.) and incubated for 4 h following the manufacturer's instructions. Absorbance was detected using an ultraviolet-spectrometer (Infinite M200, Tecan) at 490 nm to determine cell viability.

Cellular uptake—The 6-coumarin loaded-nanoparticle suspensions in medium were added into a AEC1s pre-seeded plate (5000 cells per well). After 2 h incubation, the medium was removed and the samples were washed using PBS solution. The cells were lysed with 250 μL of 1% Triton X-100 for 30 min at 37° C. Fluorescence intensity was then measured using a spectrophotometer to determine the 6-coumarin loaded nanoparticles taken up by the cells. These measurements were analyzed against an NP standard. The cell lysate sample is quantified for the total cell protein associated with the cell number using Pierce BCA protein assay for normalization with the particle uptake (Fisher Scientific, Hampton, N.H.) following manufacture's protocol. Confocal microscope was used to observe nanoparticle uptake inside the cells.

Inhalational delivery and examination of lung tissue in a rat model—The Institutional Animal Care and Use Committee of the University of Texas Southwestern Medical Center approved all procedures. Adult Sprague-Dawley rats (300-400 grams body weight) were anesthetized with an intraperitoneal injection of ketamine (50 mg/kg) and xylazine (5 mg/kg) and suspended by their front teeth on an angled fiberglass stand. The tongue was lifted with forceps and the trachea visualized using an otoscope. A 14 gauge cannula was inserted into the trachea using a guide wire. Nanoparticles were synthesized as described above, loaded with plasmid DNA vector encoding hEPOR and co-expressing GFP. Each nanoparticle preparation (1 mg) was suspended in 0.3 ml of sterile saline, sonicated (Model 300VT ultrasonic homogenizer, Biologics Inc., Manassas, Va.), aerosolized using a pediatric mesh nebulizer (Aeroneb™, 4-6 m droplets) and delivered over 3 min into the lungs via a tracheal cannula. Control rats received PLGA nanoparticles loaded with plasmid vector in the same manner. Following intubation the rats were observed to ensure complete recovery from anesthesia. At 4, 8, 14, 21, and 28 days post-treatment, rats were scarified by an overdose of Euthasol™ (pentobarbital 86 mg/kg and phenytoin 11 mg/kg by intraperitoneal injection). The lungs were inflated in situ via tracheal instillation of 4% paraformaldehyde at 25 cm $H_2O$ of airway pressure and removed intact. The fixed lobes were serially sliced at 3 mm intervals and the slice faces imaged by a biofluorescence imager (IVIS Spectrum, Caliper Life Sciences, Waltham, Mass.). Tissue blocks were embedded in paraffin, and histological sections (4 μm thickness) were examined under a fluorescent microscope (Axioscope, Carl Zeiss Microscopy, LLC, Thornwood, N.Y.).

Statistical analysis—All data are mean±standard deviation (SD). Statistical analysis was performed with Statview software using one-way ANOVA with post hoc Fisher's Protected Least Significant Difference test. $P<0.05$ was considered as significant difference.

Decellularized lung ECM and its characterization—Fresh lungs were isolated from adult pigs and processed into an ECM solution through decellularization and enzymatic digestion using sodium dodecyl sulfate (SDS) (FIG. 1) to prevent immune response, and verified by DNA residue quantification. After decellularization, 49±4 ng/mg dry weight of residual DNA was detected, which is much lower than that of native lung tissue (1113±102 ng/mg dry weight). The decellularized ECM contains two major components, collagen (77±21%) and glycosamingoglycan (GAG, 2.2±1.2 μg/mg dry weight), along with a mixture of proteins, peptides and growth factors. The collagen content is higher (11±2%), while the GAG content is lower than that in native tissue (6.0±1.9 ng/mg dry weight). After enzymatic digestion, a flowable ECM solution was obtained (FIG. 1). The enzyme treatment cut down high molecular weight proteins and de-assembled the crosslinking structure, making the ECM soluble in PBS. The diluted solution was used for coating onto nanoparticles by adsorption. The decellularization and solublization process is an established technique, and has been popular for isolating tissue-derived ECM. The main challenge is to maximally preserver biological components, especially the water-soluble bioactive molecules while completely removing cellular components that might cause an immunogenic response. As the whole process is conducted in water, some water-soluble biomacromolecules, such as GAG, would be washed away because SDS is a strong positively charged detergent that accelerates the separation of some proteins from ECM as a result of conjugation. The ECM was washed with a large amount of DI water to remove any SDS residue. The decellularized product using SDS has been evaluated in vitro and in vivo, and no cytotoxicity or significant immune response was observed from previous reports. The isolated ECM contains a complex mixture of endogenous growth factors, proteoglycans and bioactive molecules, including those detected by the investigators using a mass spectrometer (Table 1).

TABLE 1

Mass spectrometry analysis of decellularized lung ECM

| Full name | Accession No. | Protein score |
|---|---|---|
| Collagen alpha-5(IV) | XP_004022477 | 144 |
| Collagen alpha-5(IV) | XP_004022478 | 144 |
| NADH dehydrogenase | BAK19372 | 190 |
| Nuclear factor NF-kappa-B | XP_004009716 | 174 |
| Chromodomain-helicase-DNA-binding protein | XP_003757294 | 155 |
| ATP-binding cassette sub-family G member 4-like | XP_001917470 | 144 |
| Multiple epidermal growth factor-like domains protein | XP_002924008 | 143 |
| NFKB1 protein | AAI53233 | 106 |
| Copper-transporting ATPase | XP_596258 | 115 |
| Cytochrome c oxidase subunit I | YP_004935412 | 165 |
| Neutralized-like protein 4 | XP_002718856 | 136 |
| Sodium/glucose cotransporter 4 | ELK06136 | 97 |
| Acetylcholine receptor | ELK17105 | 135 |
| Retrotransposon gag domain-containing protein 1 | XP_004000841 | 146 |
| Type III secretion translocator protein | YP_004651318 | 156 |
| Glutamate synthase | WP_011645127 | 144 |
| Fatty acid synthase | YP_00686574 | 170 |
| Carbohydrate binding family protein | YP_004319456 | 143 |
| PE-PGRS family protein | YP_001850993 | 141 |
| GA27210, isoform A | XP_002137435 | 137 |

Figure 2:
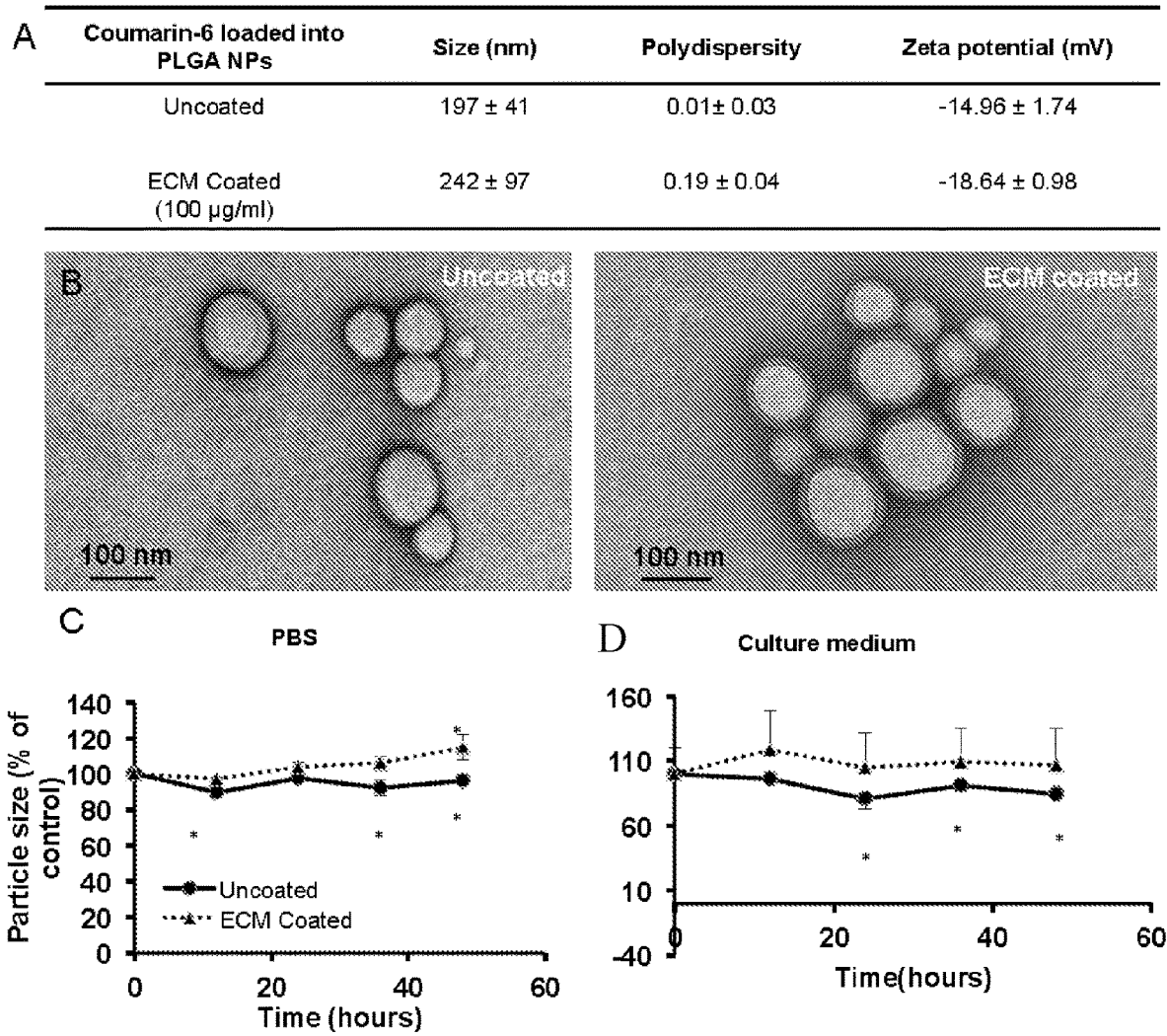
FIGS. 2A-D: Characterization of nanoparticle (NP) (FIG. 2A) size, polydispersity and zeta potential of uncoated and coated PLGA NPs.
Figure 3:
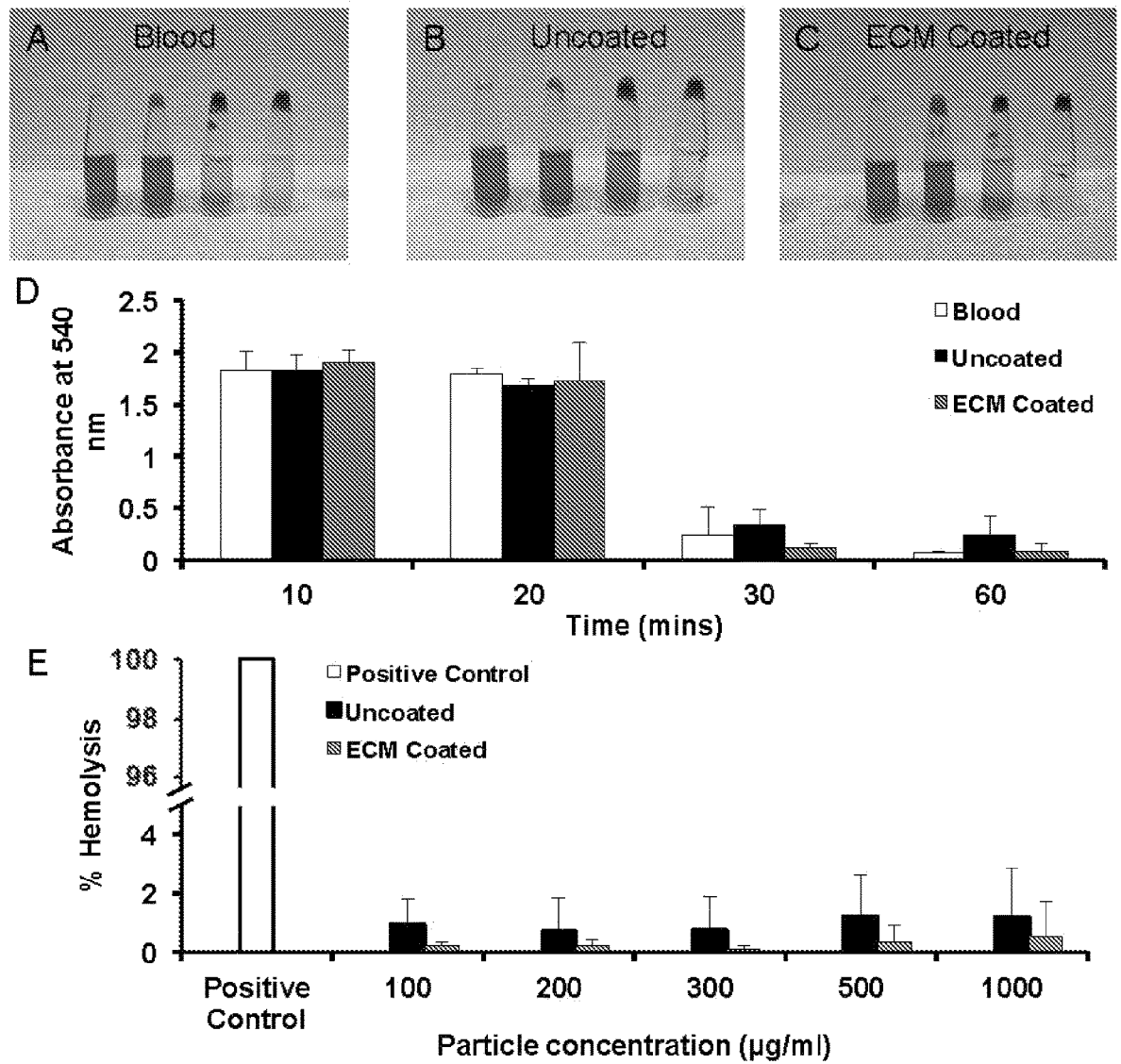
FIG. 3: Tracking soluble αKlotho transfer in the lung. C-terminal FLAG-tagged purified recombinant αKlotho (4 nmol in 200 ml) was injected intravenously into 3 normal C57/BL6 mice and the lungs were harvested 20-30 min after injection. Two control mice received injection of vehicle (saline). Exogenous αKlotho was stained with anti-FLAG antibody.

Characterization of ECM-coated PLGA nanoparticles—The inventors coated NPs with a low concentration of ECM (100 mg/mL, FIG. 2) to minimize the change in particle diameter that might alter cellular uptake characteristics. No significant difference in particle diameter and surface charge was found between uncoated (197±41 nm) and ECM coated NPs (242±97 nm) at ECM solution concentration of 100 μg/mL (FIG. 2). Increasing ECM concentration led to increased NP diameter due to physical attachment of ECM on NP surface (See FIG. 6A). Morphology under SEM demonstrates an ECM layer surrounding the coated NPs (FIG. 2B), while no layer was observed on uncoated NPs. Compared to uncoated NPs, ECM-coated NPs aggregated more easily in cell culture medium but not in PBS (FIG. 2C and FIG. 2D); there may be interactions between protein in the culture medium and the surface ECM of coated NPs.

Blood compatibility—Lung tissue has abundant vascular supply, and the NPs could penetrate the vascular wall and enter the circulation. The ECM-coated PLGA NPs show good blood compatibility similar to that of uncoated PLGA NPs, verified by the similar blood clot and hemolysis tests (FIGS. 3A-E). The hemolysis rates of NPs were very low with or without coating, indicating that the NPs do not cause hemolysis.

Figure 4:
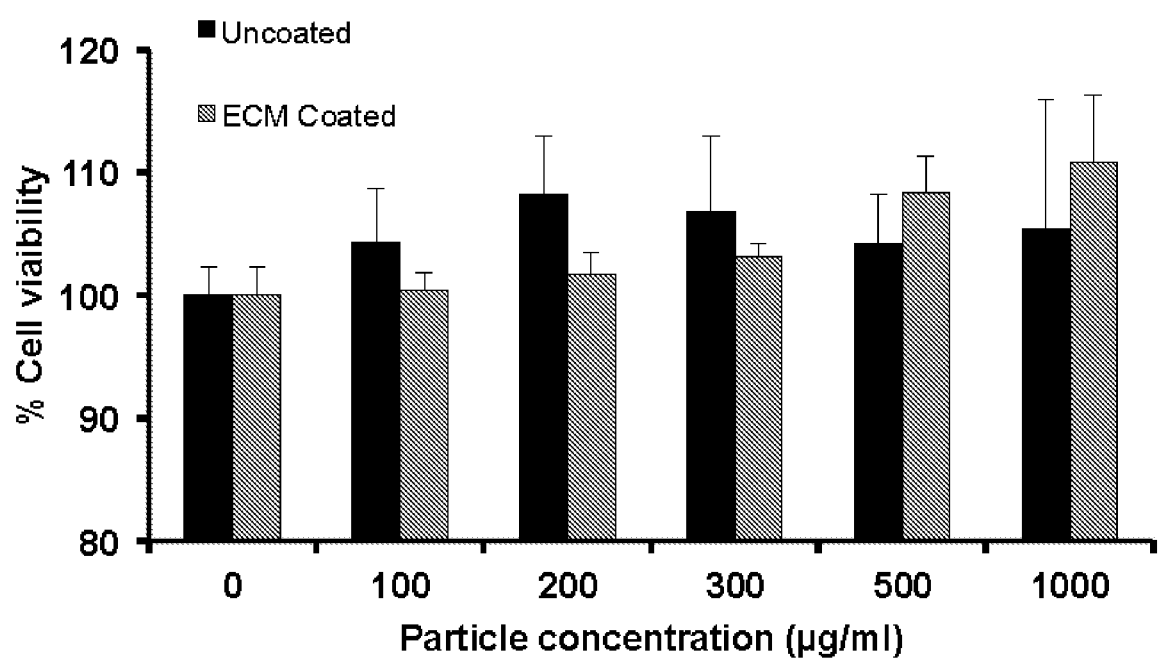
FIG. 4: In vitro cytocompatibility of uncoated and coated PLGA NPs with human type I alveolar epithelial cells (AEC1s) using MTS assay. AEC1s viability studies using an MTS assay indicated that uncoated PLGA NPs and 100 μg/ml ECM coated PLGA NPs have high cytocompatibility up to a feeding concentration of 1000 μg/ml (n=4, *p<0.05 with respect to uncoated control).

Cellular compatibility—PLGA is a popular FDA-approved biodegradable polymer. Both the polymer and its degradation products are biocompatible. The inventors previously showed that PLGA NPs are biocompatible with type I alveolar epithelial cells (Menon et al., 2014). No significant difference in cell viability was seen between ECM-coated and uncoated NPs (FIG. 4). The concentration of added NPs also has no effect on cell viability. Decellularized ECM is highly cytocompatible and may be used to accelerate skin wound healing. The combination of PLGA and ECM also exhibits high cellular compatibility.

Figure 5:
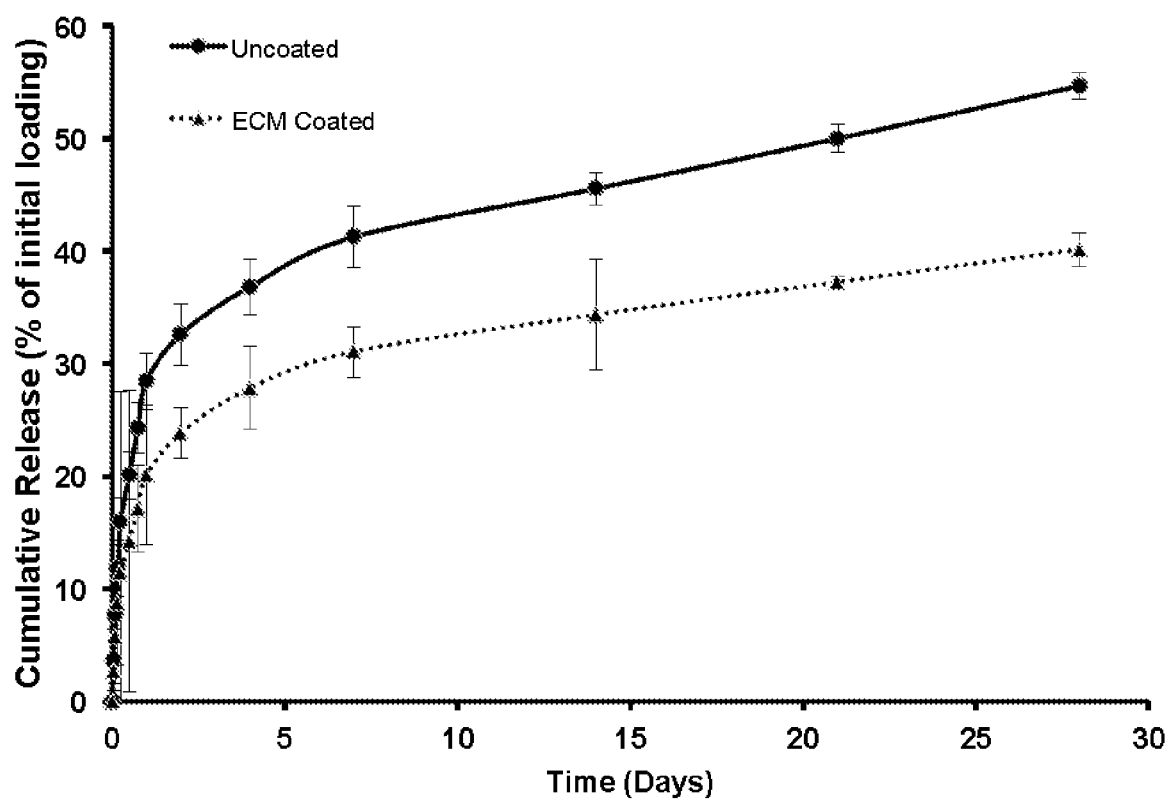
FIG. 5: In vitro release profile of encapsulated protein (Texas-Red Albumin) from ECM-coated and uncoated PLGA NPs over 28 days.

Protein release—The ECM coating extended the payload release profile of bovine serum albumin (BSA). Both ECM-coated and uncoated NPs exhibited short-term burst release on day 1 followed by slower sustained release over 28 days. ECM coating reduced burst release from ~30% to ~20%, and markedly slowed sustained BSA release compared to uncoated NPs (FIG. 5). Given that drug diffusion and carrier degradation are major factors that determine drug release kinetics, these results indicate that the ECM coating layer acted as a barrier to retard diffusion of the payload from the PLGA core. This barrier can reduce the protein loss during the transport to the site of action, and increase protein release amount at the target site.

Uptake by Lung Epithelial Cells—ECM coating greatly enhanced NP uptake in human type I alveolar epithelial cells (AEC1's) by up to ten-fold compared to uncoated NPs and collagen-coated NPs (FIG. 6B and FIG. 7A). While cellular affinity peptides, such as Arg-Gly-Asp (RGD) and transactivator of transcription (TAT), have been shown to enhance nanoparticle uptake by cells, these are the first data to show that ECM coating also enhances nanoparticle uptake. As collagen is a major component in the ECM, the inventors used pure type I collagen coating as a control, which did not significantly increase nanoparticle uptake, suggesting that other bioactive components in the ECM are responsible for facilitating nanoparticle uptake. Owing to the complex composition of the ECM solution, further studies will be needed to identify and isolate the factor(s) and the mechanisms responsible for the enhancement in uptake.

Figure 8C:
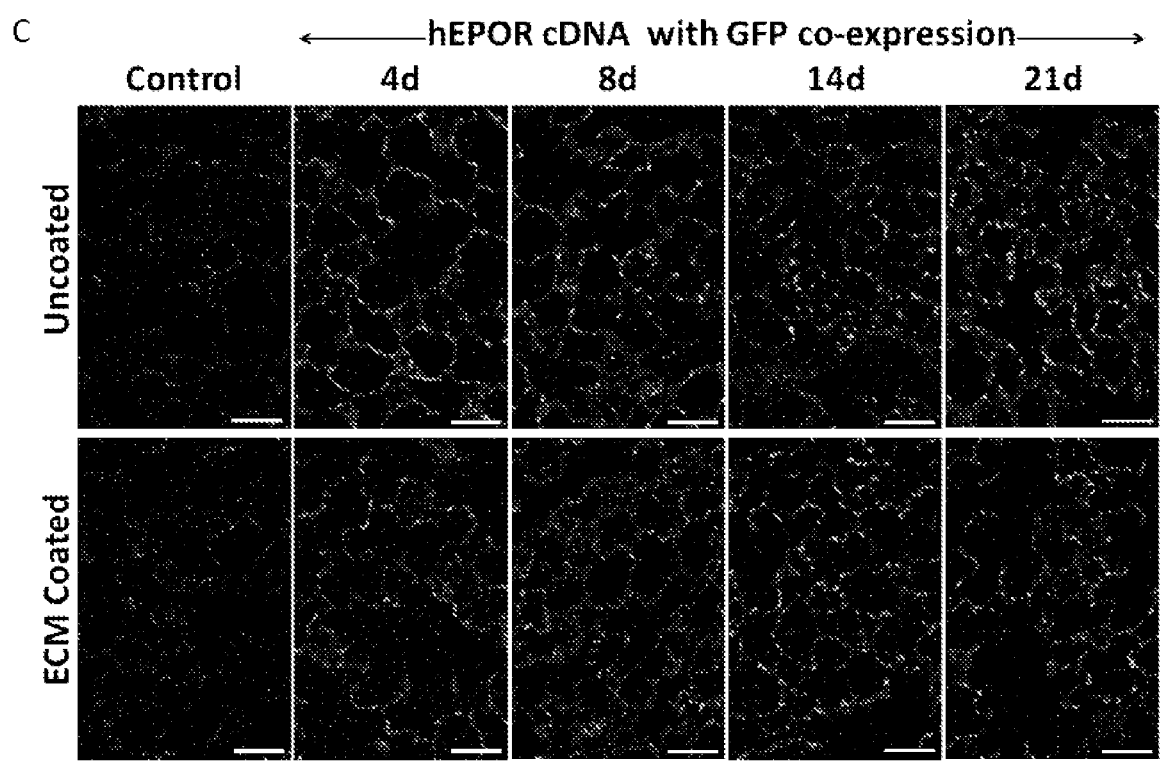

In vivo evaluation—The cDNA of human erythropoietin receptor (hEPOR), tagged with green fluorescent protein (GFP), was encapsulated into PLGA NPs. The loaded NPs were nebulized and delivered into rat lung by inhalation. Once released within the cells, the transfected cells co-express hEPOR and GFP (FIGS. 8A-C). In animals receiving uncoated PLGA NPs, GFP expression in the lung gradually increased from day 1 to day 21, consistent with slow sustained release. In ECM-coated PLGA NPs, GFP expression did not increase significantly until after day 8, with peak expression reached by day 14 followed by decline to baseline level by day 21. The delayed peak protein expression is consistent with retardation of DNA release, corresponding to the delayed release kinetics observed in vitro (FIG. 5). It is likely that the ECM coating acts as an additional barrier with slower degradation kinetics than PLGA, thus retaining the cDNA released from PLGA degradation and delaying peak protein expression in tissue. The mechanism for the shorter duration of delayed peak protein expression is not clear. The accelerated decline in fluorescent protein expression between days 14 and 21 suggests that ECM may accelerate GFP degradation. ECM is a complex substance that is known to modulate cellular metabolism and immune response as well as facilitate tissue protection and repair in vivo. Thus, ECM coating may also modulate the expression of the encapsulated gene or protein.

The inventors have developed a new approach of enhancing pulmonary cellular uptake and retention of nanoparticles for DNA delivery by inhalation to the lung. PLGA nanoparticles coated with lung-derived porcine ECM demonstrates excellent cytocompatibility and hemocompatibility with markedly enhanced particle uptake and retention by alveolar epithelial cells. Compared to uncoated nanoparticles, ECM-coated nanoparticles exhibit slower intracellular DNA release with a delayed and shorter duration of peak protein expression. These features may be useful in applications that require more precise control of the timing of delayed payload release and the in vivo effects. This methodology has potentially broad biomedical and nanotechnology applications. For example, the timing to peak drug release following administration could be customized by adjusting the ECM concentration used in coating nanoparticles.

Example 2—αKlotho Deficiency in Acute Kidney Injury Contributes to Lung Injury

Animal models—The ischemia reperfusion injury (IRI) model was conducted as previously described (Hu et al., 2010). Briefly, male Sprague-Dawley rats (250-350 g) were housed in a 12-hour light/dark cycle with free access to rodent chow and water. All animal work was conducted following the Guide for the Care and Use of Laboratory Animals by The National Institutes of Health. The Institutional Animal Care and Use Committee at UT Southwestern approved all study protocols. Under anesthesia, renal arteries were clamped with arterial clips (30 minutes) and occlusion was visually verified as blanching of the entire kidney surface. After clips were removed, the kidneys were observed for at least 5 minutes to ensure reperfusion. Sham animals underwent laparotomy of the same duration with manual manipulation of the kidneys but without arterial clamping. At predetermined times after reperfusion, blood was drawn and the kidneys harvested, instantly snap-frozen in liquid nitrogen, and stored at −80° C. for further processing. Plasma and urine chemistry of animals were analyzed using a Vitros Chemistry Analyzer (Ortho-Clinical Diagnosis, Rochester, N.Y.).

Administration of αKlotho-containing conditioned media was performed as previously described (Ravikumar et al., 2014). The animals received intraperitoneal injections of either control (100 μl) or αKlotho-containing conditioned medium CM (100 μl, ~60-100 pM, n=8) 6 hours after induction of IRI. Three days after IRI, rats were euthanized by intraperitoneal injection of Euthasol™. The left lung was perfused and snap-frozen in liquid nitrogen for the assays described below. The right lung was fixed by intra-tracheal instillation of 4% paraformaldehyde at a constant airway pressure (25 cm $H_2O$). Tissue blocks from the right caudal lobe were sampled, embedded in paraffin, sectioned (4 μm) and stained for histological evaluation.

Edema estimation—Lung tissue (~100 mg) was weighed and transferred to a platinum ashing crucible and placed on a hot plate set at 100° C. under a heat lamp for 2 h. The dried sample-containing crucible was weighed to determine the sample dry weight. The crucible was placed overnight in the ash oven set at 600° C., removed and weighed to determine the ash weight. The ash was dissolved in 2 mL of HCl and the $Na^+$ content measured by flame photometry.

Cell culture—Human lung epithelial cells (A549, American Type Culture Collection, Manassas, Va.) were grown in Dulbecco's Modified Eagle Medium (DMEM)-nutrient mixture F12 (Life Technologies, Grand Island, N.Y.) with 1% L-glutamine. An in vitro oxidative stress model using hydrogen peroxide ($H_2O_2$) and modified from one the inventors employed for in kidney cells (Panesso et al., 2014) was used to study the cytoprotective effects of αKlotho.

Biochemical assays—Cell injury—Lactate dehydrogenase (LDH) cytotoxicity detection kit (Clontech Laboratories, Mountain View, Calif.) was used to measure release of cytoplasmic LDH into the culture supernatant. LDH generates NADH from lactate, which reacts with diaphorase to generate formazan dye products (absorbance 490 nm).

Total antioxidant capacity—Both copper- and iron-based assays were performed. Copper reducing equivalents were measured using a calorimetric assay (OxiSelect™, Cell BioLabs, San Diego, Calif.). The Trolox antioxidant assay (Sigma-Aldrich, St. Louis, Mo.) is based on formation of a ferryl myoglobin radical from metmyoglobin and hydrogen peroxide, which oxidizes ABTS (2,2'-azino-bis(3-ethylbenzthiazoline-6-sulfonic acid) to ABTS, a soluble chromogen. Trolox, a water-soluble vitamin E analog, serves as a standard control antioxidant.

Antioxidant Reporter—A dual-luciferase assay (Cignal, SA Biosciences, Valencia, Calif.) was used to measure the activity of Nrf-1 and -2 (nuclear factor E2-related factor) transcription factor activation of tandem antioxidant response elements (ARE's) regulating genes that protect cells from oxidative damage. The ARE reporter contains inducible antioxidant responsive firefly luciferase construct and constitutively expressed *Renilla* luciferase construct. Upon transfection with the ARE reporter, the activities of the firefly and *Renilla* luciferases quantify transcriptional activities of the antioxidant response pathway.

Oxidative damage—8-hydroxydeoxyguanosine (8-OHdG) was used as a marker of oxidative DNA injury. DNA was extracted using DNAzol (Life Technologies, Grand Island, N.Y.), precipitated in 100% ethanol, washed with 70% ethanol, suspended in 8 mM NaOH, and the 8-OHdG concentration determined by ELISA (OxiSelect™ Cell BioLabs, San Diego, Calif.) compared against a 8-OHdG standard curve. Protein Carbonyl was measured by ELISA (OxiSelect™ Cell BioLabs, Inc. San Diego, Calif.) was used to measure protein oxidation against a known reduced/oxidized BSA standard curve. 8-isoprostane was measured by EIA (Cayman Chemical, Ann Arbor, Mich.) as a marker for lipid oxidation, based on the competitive binding between 8-isoprostane and 8-isoprostane-acetylcholinesterase (AChE) conjugate (8-Isoprostane Tracer) for limited specific binding sites.

Conditioned medium and recombinant αKlotho—Two types of αKlotho preparations were used. Conditioned media containing αKlotho were prepared as previously described (Ravikumar et al., 2014). Briefly, Chinese hamster ovary (CHO) cells were stably transfected with soluble αKlotho or vector. Serum-free media was added 16 hrs post-transfection and after another 16 hrs, media was collected and stored at −80° C. The conditioned medium contained recombinant soluble Klotho along with other secreted proteins from the CHO cells. The control media was obtained from CHO cells transfected with only the expression plasmid.

The inventors also used purified recombinant αKlotho. Human or murine soluble αKlotho was cloned into pEF1/Myc-His/A vector (Invitrogen) and transfected into suspension Free Style 293-F cells (Invitrogen). To establish single stable cell line that expressed recombinant protein, cells were selected in 500 g/ml G418 (Gibco). Single clones of stable αKlotho-expressing cells were cultured in serum-free medium (SFM) (Invitrogen) with 100 μg/ml G418 and 10% Pluronic F-68. The condition media were collected at suspension cell density ~300×$10^4$ and centrifuged at 15,000×g for 30 mins at 4° C. to remove cell debris. The supernatant was mixed with Ni-NTA resin (Thermo) that was pre-equilibrated with 20 mM phosphate, pH 7.4, 300 mM NaCl. After incubation at 1 hour at room temperature, the Ni-NTA resin was packed into the Econo-column and washed with the above buffer (35× column volume). Bound αKlotho was eluted by 50-250 mM imidazole. The highest concentration αKlotho protein was eluted at second fraction by 50 mM imidazole. The protein quality was checked by SDS-PAGE and Coomassie blue staining with a BSA standard.

Quantitatitative PCR of potential Nrf-1 and -2 anti-oxidant targets—Total RNA was extracted with RNeasy Mini kit (Qiagen, Germantown, Md.) from A549 cells according to the manufacturer's protocol. Complementary DNA (cDNA) was generated with oligo-dT primers (SuperScript III First Strand Synthesis System, Invitrogen). Primers used for detection of variety of genesare shown in Table 2. Briefly, PCR was performed in an ABI Prism 7000 Sequence Detector (Applied BioSystems, Foster City, Calif.), with one cycle (95° C.×10 min) and then 40 cycles (95° C.×15 s and 60° C.×1 min) in triplicate for each sample. PCR products were verified by gel electrophoresis. The cycle threshold (Ct) values of the target gene transcript levels were analyzed and normalized to Ct of β actin. The relative abundance of target gene transcript was represented by the $2^{-\Delta\Delta ct}$ versus control group.

TABLE 2

Primer pairs used in PCR-based sequencing

| | | Primer sequences (5'-3') | |
|---|---|---|---|
| Transcript | | Forward | Reverse |
| HMOX1 | Heme oxygenase 1 | tctcttggctggcttcctta (SEQ ID NO: 1) | attgcctggatgtgcttttc (SEQ ID NO: 2) |
| HMOX2 | Heme oxygenase 2 | gaaggaagggaccaaggaag (SEQ ID NO: 3) | gtggccagcttaaacagctc (SEQ ID NO: 4) |
| SOD1 | Superoxide dismutase | ggcaaaggtggaaatgaaga (SEQ ID NO: 5) | gggcctcagactacatccaa (SEQ ID NO: 6) |
| GSS | Gluthathione synthase | gcctcctacatcctcatgga (SEQ ID NO: 7) | aaagatgcccagctctgaaa (SEQ ID NO: 8) |
| MT1A | Methalothionine 1A | gcaaatgcaaagagtgcaaa (SEQ ID NO: 9) | cagctgcacttctctgatgc (SEQ ID NO: 10) |

TABLE 2 -continued

Primer pairs used in PCR-based sequencing

| | Transcript | Primer sequences (5'-3') | |
|---|---|---|---|
| | | Forward | Reverse |
| MT2A | Methalothionine 1A | caacctgtcccgactctagc (SEQ ID NO: 11) | aggagcagcagcttttcttg (SEQ ID NO: 12) |
| TXNRD1 | Thioredoxin reductase | agagaggaaggcaggtgtca (SEQ ID NO: 13) | ctggacttcctgcttcttgg (SEQ ID NO: 14) |
| GRX | Glutaredoxin | aacggtgcctcgagtcttta (SEQ ID NO: 15) | caattgggtcctgtgacctt (SEQ ID NO: 16) |
| HYOU1 | Hypoxia up-regulated 1 | gccattgtcaaacctggagt (SEQ ID NO: 17) | aacgtagcgtagcctttgga (SEQ ID NO: 18) |
| NQO1 | NAD(P)H dehydrogenase, quinone 1 | gcttcaaatggcagaaaagc (SEQ ID NO: 19) | agaacccatcgaccatcaag (SEQ ID NO: 20) |
| PRDX1 | Peroxiredoxin 1 | tggggtcttaaaggctgatg (SEQ ID NO: 21) | tccccatgtttgtcagtgaa (SEQ ID NO: 22) |
| PRDX2 | Peroxiredoxin 2 | gtgtccttcgccagatcact (SEQ ID NO: 23) | acgttgggcttaatcgtgtc (SEQ ID NO: 24) |
| PRDX3 | Peroxiredoxin 3 | gccgttgtcaatggagagtt (SEQ ID NO: 25) | tccactgagactgcgacaac (SEQ ID NO: 26) |
| PRDX5 | Peroxiredoxin 5 | acggtgcagtgaaggagagt (SEQ ID NO: 27) | aacagctctgccaggttcac (SEQ ID NO: 28) |
| PRDX6 | Peroxiredoxin 6 | ggatggggatagtgtgatgg (SEQ ID NO: 29) | ctgacatcctctggctcaca (SEQ ID NO: 30) |
| TXNDC12 | Thioredoxin domain containing 12 | cacagagcacttgcggttta (SEQ ID NO: 31) | gcaggctctggctcaaatac (SEQ ID NO: 32) |
| TXNDC17 | Thioredoxin domain containing 17 | agaggggctgaagcacatta (SEQ ID NO: 33) | caggttggcctgaagacact (SEQ ID NO: 34) |
| TXNDC5 | Thioredoxin domain containing 5 | tgtggctcctgagttgagtg (SEQ ID NO: 35) | tcaatctgctccatgctacg (SEQ ID NO: 36) |
| PXDN | Peroxidasin | ttgcgactggactcaaacac (SEQ ID NO: 37) | ggcctttcacagttcagctc (SEQ ID NO: 38) |

Results

ALI in AKI—The inventors used an established model of ischemia-reperfusion injury (IRI) (Hu et al., 2010) and confirmed a markedly reduced circulating αKlotho level in the animals with AKI (FIGS. 9A-B). Histologically, the lung in AKI exhibited smaller distal air spaces, thicker alveolar walls, and cellular exudation into the air spaces (FIG. 9B). The Na+/dry lung weight ratio was elevated consistent with interstitial edema (FIG. 9B). The lungs from AKI animals showed generalized oxidative damage of DNA, protein, and lipids (FIG. 10B), which is consistent with heightened oxidative stress to the lungs in AKI in a manner similar to that described by the inventors in direct lung injury caused by acute hyperoxia exposure (Ravikumar et al., 2014).

Total Antioxidant Capacity:

Role of αKlotho—The inventors previously found severe acute systemic αKlotho deficiency in this AKI model (Hu et al., 2010). The reperfusion phase post renal ischemia is a highly oxidative state (Gao et al., 2014; Kasuno et al., 2014). The inventors have shown αKlotho protects against acute hyperoxic stress in the lung (Ravikumar et al., 2014). The above observations in concert highly suggest that the acute αKlotho deficiency in AKI contributes to ALI. To take the status of these findings from correlation to causality, the inventors replenished the αKlotho deficiency in AKI with exogenous Klotho and queried whether the lung involvement is alleviated.

αKlotho repletion beyond 4 hours post-IRI does not affect the peak plasma creatinine or creatinine clearance but αKlotho replacement when given early will alleviated AKI [25]. By administering αKlotho 6 hrs after AKI, we did not change the course of AKI (FIG. 9B) and succeeded in repletion of the αKlotho deficiency (FIG. 9A).

αKlotho administration reduced the histologic changes, edema, (FIG. 9C) and oxidative damage to DNA, protein and lipids in the lungs of AKI rats (FIG. 10A). These effects occurred with no change in serum creatinine (FIG. 9B) thus dissociating the lung effect from renoprotection by αKlotho. This interventional approach strongly supports that the αKlotho deficiency in AKI is not mere associative but actually pathogenic for the ALI.

Direct effect on pulmonary epithelia—The animal experiments above are important proof-of-principle studies showing that αKlotho deficiency exacerbates pulmonary injury and put forward promising therapeutic potentials in the horizon. However, the complexities of the intact organism preclude the ability to conclude that αKlotho has a direct action on pulmonary epithelia and renders the dissection of cytoprotective mechanism rather difficult. To this end, the inventors used cultured pulmonary epithelial cells, simulated the post-AKI oxidative milieu with hydrogen peroxide ($H_2O_2$), and examined if αKlotho can ameliorate oxidative damage (see below).

One may question the relevance of the experiment where αKlotho is directly added to lung epithelial cells. Can a 130 kD protein leave the pulmonary vasculature readily to access the alveolar cells? The inventors have shown that while αKlotho cannot traverse the glomerular capillary, it crosses the peritubular capillary freely to be taken up by the tubule in surprisingly short time (Hu et al., 2015). The inventors tested if this can be achieved in the pulmonary capillaries. Exogenously injected FLAG-tagged Klotho is present inside the capillaries but also clearly detectable in the lung in the interstitial space outside the capillaries in 30 mins after injection (FIG. 11).

Cytoprotection via anti-oxidation—The inventors dosed $H_2O_2$ to establish the conditions of moderate oxidative stress and cell damage (FIG. 12A). The elevated oxidative damage markers in the lung in AKI are ameliorated by treatment with αKlotho. To examine if this is a direct effect of αKlotho on lung epithelia, we added purified αKlotho directly to a lung epithelial cell line and tested whether it protects against $H_2O_2$ toxicity. We previously showed that αKlotho transfection and αKlotho-conditioned media prevent cell death from 95% hyperoxic $O_2$ insult (Ravikumar et al., 2014) but that system did not permit us to assess what concentration of αKlotho is required for cytoprotection and whether it is in the same order of magnitude as circulating αKlotho. We now use purified recombinant αKlotho to define the dose range of αKlotho required. Hydrogen peroxide induced damage in A549 cells in a dose-dependent fashion (FIG. 12A). Protection by recombinant Klotho was detectable at 25 pM and maximal response was attained around 200 pM (FIG. 12B). The range where therapeutic efficacy is observed in fact is in the same order of magnitude as circulating αKlotho concentrations in humans and rodents (Hu et al., 2015; Barker et al., 2015).

The inventors have previously shown that heme oxygenase-1 (HOX-1) is increased by αKlotho-containing conditioned media in the lung (Ravikumar et al., 2014), and HOX-1 is a downstream effect of the nrf-2 pathway. They next performed a dose-response of purified αKlotho on a nrf-2 promoter reporter and showed that purified αKlotho activates Nrf-2.

Example 3—Solubilized Lung-Derived Extracellular Matrix Mitigates Hyperoxic Lung Injury Decellularized extracellular matrix (ECM) contains a complex cocktail of tissue-specific bioactive components that work in concert to promote cellular homeostasis, and has been used as a scaffold for bioengineered organs or as a substrate to promote wound healing. To examine whether lung-derived ECM could mitigate acute lung injury, fresh porcine lung was decellularized and engineered into a clear solution (3 mg/ml). Sprague-Dawley rats (body weight~300 g) received the ECM solution (1.5 mg) or placebo (saline) (n=4 each) via one of two protocols: a) direct tracheal instillation followed by continuous hyperoxia (90% $O_2$ for 3 days), or b) nebulization through a tracheal cannula followed by intermittent hyperoxia (90% $O_2$ for 24 h alternating with normoxia [21% $O_2$] for 24 h) for a total of 6 days. Age-matched untreated control animals were exposed to normoxia. Lung tissue was harvested for histology and assays of apoptosis (caspase-8 activity, nmole/hr/µg protein) and oxidative damage to DNA (8-hydroxydeoxyguanosine, 8-OHdG, ng/ml), lipid (8-isoprostane, pg/ml) and protein (carbonyl, mmoles/mg). Results (mean±SD) were compared among groups by ANOVA. P<0.05: * vs. placebo; † vs. 21% $O_2$. Results are shown below in Table 3.

TABLE 3

ECM Results

| | Normoxia | Instillation Continuous Hyperoxia | | Nebulization Intermittent Hyperoxia | |
|---|---|---|---|---|---|
| Treatment | None | Placebo | ECM | Placebo | ECM |
| 8-OHdG | 0.08 ± 0.01 | 0.15 ± 0.01 † | 0.11 ± 0.01 *† | 0.14 ± 0.01 † | 0.13 ± 0.01 † |
| Caspase-8 | 8.80 ± 0.57 | 16.09 ± 0.52 † | 13.80 ± 0.74 *† | 19.75 ± 0.55 † | 17.33 ± 0.53 *† |
| 8-Isoprostane | 2.67 ± 0.41 | 8.58 ± 0.77 † | 6.41 ± 3.14 *† | 8.21 ± 1.08 † | 7.41 ± 0.22 † |
| Carbonyl | 2.30 ± 0.12 | 3.61 ± 0.07 † | 3.36 ± 0.07 *† | 3.61 ± 0.12† | 3.28 ± 0.12 *† |

As shown above, most oxidative damage markers were more elevated following continuous than intermittent hyperoxia. ECM treatment attenuated hyperoxia-induced damage to DNA (5 and 28%), apoptosis (12 and 14%), lipid (10 and 25%) and protein oxidation (7 and 9%) compared to placebo in the intermittent and continuous hyperoxia groups, respectively. We conclude that targeted delivery of decellularized ECM to the lung modestly alleviated acute oxidant lung damage.

Example 4—Alpha-Klotho Protects Zucker Diabetic Fatty Rat Lung Against Hyperoxic Injury Systemic delivery of αKlotho protein has been observed to protect normal rat lungs from oxidant damage (*Am J Physiol Lung Cell Mol Physiol*. 307(7):L566-75, 2014). To determine whether targeted delivery of αKlotho cDNA mitigates oxidant lung injury in the presence of elevated basal metabolic lipo-oxidative stress in the Zucker Diabetic Fatty (ZDF fa/fa) rats, the inventors delivered nebulized αKlotho cDNA (25 µg) or empty vector (control) to anesthetized male fa/fa and lean control (+/+) rats (350-400 g body weight) via a tracheal cannula (n=6-9 per group). Two days after inhalation, animals were exposed to hyperoxia (90% $O_2$) in an environmental chamber for 3 d. Age-matched, untreated control animals were exposed to normoxia (21% $O_2$). Lung tissue was analyzed for histology and assays of oxidative damage to DNA (8-hydroxydeoxyguanosine, 8-OHdG, ng/ml), lipid (8-isoprostane, pg/ml) and protein (carbonyl, mmoles/mg). Results are shown below in Table 4.

TABLE 4

| | Alpha-Klotho Results | | | | | |
|---|---|---|---|---|---|---|
| | Exposure | | | | | |
| | 21% $O_2$ | | 90% $O_2$ | | | |
| | | | Treatment | | | |
| | None | | Plasmid vector | | αKlotho cDNA | |
| Genotype | +/+ | fa/fa | +/+ | fa/fa | +/+ | fa/fa |
| 8-OHdG | 0.08 ± 0.01 | 0.11 ± 0.01* | 0.19 ± 0.01† | 0.23 ± 0.01*† | 0.12 ± 0.01†‡ | 0.15 ± 0.01*†‡5 |
| 8-Isoprostane | 2.50 ± 0.20 | 3.05 ± 0.13* | 7.71 ± 0.42† | 10.10 ± 1.17*† | 4.08 ± 0.45†‡ | 4.90 ± 0.49*†‡ |
| Carbonyl | 2.29 ± 0.16 | 2.53 ± 0.08* | 3.59 ± 0.07† | 3.85 ± 0.07*† | 2.98 ± 0.19†‡ | 3.18 ± 0.12*†‡ |

Results (mean ± SD) were compared among groups by ANOVA.
P < 0.0001:
*vs. fa/fa with same $O_2$ exposure and treatment;
†vs. normoxia in the same genotype;
‡vs. vector in the same genotype and $O_2$ exposure.

Regardless of $O_2$ exposure or treatment, DNA damage, lipid and protein oxidation markers were modestly but significantly elevated (21-37%, 20-39% and 7-11% respectively) in fa/fa animals compared to lean controls indicating heightened oxidative stress. Inhalation of αKlotho cDNA significantly attenuated hyperoxia-induced oxidative damage to DNA (~36%), lipid (~50%) and protein (~17%) and preserved alveolar morphology to a similar extent in both genotypes. The targeted upregulation of αKlotho expression in the lung was observed to protect against acute oxidant lung damage in both fa/fa and +/+ animals, supporting the use of this therapeutic approach for the treatment of lung injury.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

U.S. Pat. No. 5,725,871
U.S. Pat. No. 5,756,353
U.S. Pat. No. 5,780,045
U.S. Pat. No. 5,804,212
Ahmad et al., *International journal of antimicrobial agents,* 26, (4), 298-303, 2005.
Ahmad et al., Reduction in burst release after coating poly(D,L-lactide-co-glycolide) (PLGA) microparticles with a drug-free PLGA layer, *Pharm Dev Technol.* 2012 January-February; 17(1):66-72. doi: 10.3109/10837450.2010.513989. Epub 2010 Sep. 20.
Azarmi, S.; Roa, W. H.; Lobenberg, R. Advanced drug delivery reviews, 60, (8), 863-75, 2008.
Bader et al., *European journal of cardio-thoracic surgery: official journal of the European Association for Cardio-thoracic Surgery,* 14, (3), 279-84, 1998.
Badylak et al., *Acta biomaterialia,* 5, (1), 1-13, 2009.
Badylak, S. F. *Biomaterials,* 28, (25), 3587-93, 2007
Barker et al., The demonstration of alphaKlotho deficiency in human chronic kidney disease with a novel synthetic antibody. *Nephrol Dial Transplant,* 30(2):223-233, 2015.
Basu and Wheeler, Effects of ischemic acute kidney injury on lung water balance: nephrogenic pulmonary edema? *Pulm Med,* 414253, 2011.
Benders, K. E.; van Weeren, P. R.; Badylak, S. F.; Saris, D. B.; Dhert, W. J.; Malda, J. *Trends in biotechnology,* 31, (3), 169-76, 2013.
Blank V., Small Maf proteins in mammalian gene control: mere dimerization partners or dynamic transcriptional regulators? *J Mol Biol,* 376(4):913-925, 2008.
Bloch et al., Klotho is a substrate for alpha-, beta- and gamma-secretase. FEBS Lett, 583(19):3221-3224, 2009.
Booth et al., *The Journal of heart valve disease* 11, (4), 457-62, 2002.
Brown and Badylak, *Translational research: the journal of laboratory and clinical medicine,* 163, (4), 268-85, 2014.
Chase and Wheeler, Disorders of the Pediatric Chest. In: Wheeler D S, Wong H R, Shanley T P, eds. *Pediatric Critical Care Medicine: Basic Science and Clinical Evidence.* 1 ed. Springer-Verlag New York, LLC.: New York; 2007.
Chen et al., Insulin stimulates the cleavage and release of the extracellular domain of Klotho by ADAM10 and ADAM17. *Proc Natl Acad Sci USA,* 104(50):19796-19801, 2007.
Chertow et al., Prognostic stratification in critically ill patients with acute renal failure requiring dialysis. *Arch Intern Med,* 155(14): 1505-1511, 1995.
Cullinan et al., Nrf2 is a direct PERK substrate and effector of PERK-dependent cell survival. *Mol Cell Biol,* 23(20): 7198-7209, 2003.
Danhier et al., *Journal of Controlled Release,* Volume 161, Issue 2, 20: Pages 505-522, 2012.
Daum et al., [Diffusion capacity of the lung in patients with uremia]. Cas Lek Cesk, 104(47):1285-1290, 1965.

Doi et al., Lung injury following acute kidney injury: kidney-lung crosstalk. *Clin Exp Nephrol*, 15(4):464-470, 2011.

Dvorak and Feng, The vesiculo-vacuolar organelle (VVO). A new endothelial cell permeability organelle. *J Histochem Cytochem*, 49(4):419-432, 2001.

Enayati et al., Modification of the release characteristics of estradiol encapsulated in PLGA particles via surface coating, *Ther Deliv.*, 3(2):209-26, February 2012.

Faubel S. Pulmonary complications after acute kidney injury. *Adv Chronic Kidney Dis*, 15(3):284-296, 2008.

Faulk et al., *Journal of cellular physiology*, 229, (8), 984-9, 2014.

Feng et al., Ultrastructural studies define soluble macromolecular, particulate, and cellular transendothelial cell pathways in venules, lymphatic vessels, and tumor-associated microvessels in man and animals. *Microsc Res Tech*, 57(5):289-326, 2002.

Fields et al., Surface modified poly(β amino ester)-containing nanoparticles for plasmid DNA delivery, *J Control Release*. 2012 Nov. 28; 164(1):41-8. doi: 10.1016/j.jconrel. 2012.09.020. Epub 2012 Oct. 5.

Foldbjerg et al., *Chemico-biological interactions*, 204, (1), 28-38, 2013.

Fontana et al., Amoxicillin-loaded polyethylcyanoacrylate nanoparticles: influence of PEG coating on the particle size, drug release rate and phagocytic uptake, *Biomaterials.*, 22(21):2857-65, November 2001.

Gao et al., TRPM2 mediates ischemic kidney injury and oxidant stress through RAC1, *Journal of Clinical Investigation*, 124(11), 4989-5001, 2014.

Hadinoto et al., *International journal of pharmaceutics*, 333, (1-2), 187-98, 2007.

Hassoun et al., Kidney ischemia-reperfusion injury induces caspase-dependent pulmonary apoptosis. *Am J Physiol Renal Physiol*, 297(1):F125-137, 2009.

Horiguchi et al., *Journal of controlled release: official journal of the Controlled Release Society*, 187, 167-74, 2014.

Hsieh and Papaconstantinou, The effect of aging on p38 signaling pathway activity in the mouse liver and in response to ROS generated by 3-nitropropionic acid. *Mech Ageing Dev*, 123(11):1423-1435, 2002.

Hu and Moe, Klotho as a potential biomarker and therapy for acute kidney injury. *Nat Rev Nephrol*, 8(7):423-429, 2012.

Hu et al., Klotho deficiency is an early biomarker of renal ischemia-reperfusion injury and its replacement is protective. *Kidney Int*, 78(12):1240-1251, 2010.

Hu et al., Klotho: a novel phosphaturic substance acting as an autocrine enzyme in the renal proximal tubule. *FASEB J*, 24(9):3438-3450, 2010.

Hu et al., Klotho deficiency causes vascular calcification in chronic kidney disease. *J Am Soc Nephrol*, 22(1):124-136, 2011.

Hu et al., Secreted klotho and chronic kidney disease. *Adv Exp Med Biol*, 728:126-157, 2012.

Hu et al., Fibroblast growth factor 23 and Klotho: physiology and pathophysiology of an endocrine network of mineral metabolism. *Annu Rev Physiol*, 75:503-533, 2013a.

Hu et al., Renal and extrarenal actions of Klotho. *Semin Nephrol* 33(2):118-129, 2013b.

Hu et al., The erythropoietin receptor is a downstream effector of Klotho-induced cytoprotection. *Kidney Int*, 84(3):468-481, 2013c.

Hu et al., Renal production, uptake, and handling of circulating alpha-Klotho. *J Am Soc Nephrol*. In Press, May 14, 2015.

Ikushima et al., Anti-apoptotic and anti-senescence effects of Klotho on vascular endothelial cells. *Biochem Biophys Res Commun*, 339(3):827-832, 2006.

Imura et al., Secreted Klotho protein in sera and CSF: implication for post-translational cleavage in release of Klotho protein from cell membrane. FEBS Lett, 565(1-3):143-147, 2004.

Ingenito et al., *Journal of tissue engineering and regenerative medicine*, 4, (4), 259-72, 2010.

Itoh et al., An Nrf2/small Maf heterodimer mediates the induction of phase II detoxifying enzyme genes through antioxidant response elements. *Biochem Biophys Res Commun*, 236(2):313-322, 1997.

Jones et al., *International journal of pharmaceutics*, 236, (1-2), 65-79, 2002.

Jones et al., *The Journal of pharmacy and pharmacology*, 54, (8), 1065-72, 2002.

Karacan et al., Pulmonary function in uremic patients on long-term hemodialysis. *Ren Fail*, 26(3):273-278, 2004.

Kasuno et al., Renal redox dysregulation in AKI: application for oxidative stress marker of AKI, *American Journal of Physiology. Renal Physiology*, 307(12), F1342-F1351, 2014.

Kelleher and Vacanti, *Journal of the Royal Society, Interface/the Royal Society*, 7 Suppl 6, S717-29, 2010.

Kelly K J. Distant effects of experimental renal ischemia/reperfusion injury. *J Am Soc Nephrol*, 14(6):1549-1558, 2003.

Klein et al., Interleukin-6 mediates lung injury following ischemic acute kidney injury or bilateral nephrectomy. *Kidney Int*, 74(7):901-909, 2008.

Kramer et al., Renal ischemia/reperfusion leads to macrophage-mediated increase in pulmonary vascular permeability. *Kidney Int*, 55(6):2362-2367, 1999.

Ku et al., *Journal of nanoscience and nanotechnology*, 8, (6), 2971-8, 2008.

Kumar et al., *Cell transplantation*, 20, (5), 609-18, 2011.

Kuro-o et al., Mutation of the mouse klotho gene leads to a syndrome resembling ageing. *Nature*, 390(6655):45-51, 1997.

Kuro-o M., Klotho as a regulator of oxidative stress and senescence. *Biol Chem*, 389(3):233-241, 2008.

Kurosu et al., Suppression of aging in mice by the hormone Klotho. *Science*, 309(5742):1829-1833, 2005.

Levy et al., The effect of acute renal failure on mortality. A cohort analysis. JAMA, 275(19):1489-1494, 1996.

Levy, L A, Severe hypophosphatemia as a complication of the treatment of hypothermia. *Arch Intern Med*, 140(1): 128-129, 1980.

Lin et al., *Tissue engineering* 10, (7-8), 1046-53, 2004.

Lin et al., *Tissue engineering. Part A*, 16, (5), 1515-26, 2010.

Lindberg et al., The kidney is the principal organ mediating klotho effects. *J Am Soc Nephrol*, 25(10):2169-2175, 2014.

Liu et al., *Biomaterials* 30, (23-24), 3865-73, 2009.

Matsumura et al., Identification of the human klotho gene and its two transcripts encoding membrane and secreted klotho protein. *Biochem Biophys Res Commun*, 242(3): 626-630, 1998.

Medberry et al., *Biomaterials.*, 34(4):1033-40, 2013.

Menon et al., *Journal of biomedical materials research. Part A*, 100, (8), 1998-2005, 2012.

Menon et al., Polymeric nanoparticles for pulmonary protein and DNA delivery. *Acta Biomaterialia*, 10:2643-2652, PMCID: PMC4008694, 2014.

Motohashi et al., Integration and diversity of the regulatory network composed of Maf and CNC families of transcription factors. *Gene*, 294(1-2): 1-12, 2002.

Murray and Lopez, *Lancet*, 349, (9064), 1498-504, 1997.

Nath and Norby, Reactive oxygen species and acute renal failure. *Am J Med*, 109(8):665-678, 2000.

Osburn et al., Increased colonic inflammatory injury and formation of aberrant crypt foci in Nrf2-deficient mice upon dextran sulfate treatment. *Int J Cancer*, 121(9): 1883-1891, 2007.

Paladino et al., Acute kidney injury and lung dysfunction: a paradigm for remote organ effects of kidney disease? *Microvasc Res*, 77(1):8-12, 2009.

Pandey et al., *The Journal of antimicrobial chemotherapy*, 52, (6), 981-6, 2003.

Panesso et al., Klotho has dual protective effects on cisplatin-induced acute kidney injury. *Kidney Int*, 85(4):855-870, 2014.

Rabb et al., Acute renal failure leads to dysregulation of lung salt and water channels. *Kidney Int*, 63(2):600-606, 2003.

Rabe et al., Global Initiative for Chronic Obstructive Lung, D. *American journal of respiratory and critical care medicine*, 176, (6), 532-55, 2007.

Rakugi et al., Anti-oxidative effect of Klotho on endothelial cells through cAMP activation. *Endocrine*, 31(1):82-87, 2007.

Ravikumar et al., Alpha-klotho protects against oxidative damage in pulmonary epithelia. p. In revision, 2013.

Ravikumar et al., alpha-Klotho protects against oxidative damage in pulmonary epithelia. *Am J Physiol Lung Cell Mol Physiol*, 307(7):L566-575, 2014.

Ravikumar P, J F Ye, M Shi, L Li, M Taniguchi, J Zhang, M Kuro-o, MC Hu, O W Moe, CCW Hsia. Alpha-Klotho deficiency in acute kidney injury contributes to lung damage. *J Appl Physiol* (1985) 120:72-732, 2016a.

Ravikumar et al., Nanoparticle facilitated inhalational delivery of erythropoietin receptor cDNA protects against hyperoxic lung injury, *Nanomedicine* 12(3):811-21, 2016b.

Rees et al. "The importance of particle size in responses to inhaled bronchodilators." *Eur J Respir Dis*, 63(Suppl): 73-78, 1982.

*Remington's Pharmaceutical Sciences*, 18th Ed. Mack Printing Company, pp. 1289-1329, 1990.

*Remington: The Science and Practice of Pharmacy*, 21$^{st}$ Ed., Lippincott Williams and Wilkins, 2005.

Rubenfeld et al., Incidence and outcomes of acute lung injury. *New Engl J Med.*, 353:1685-93, 2005.

Sawkins et al., *Acta Biomater.*, 9(8):7865-73, 2013.

Seeley, E J, Updates in the management of acute lung injury: a focus on the overlap between AKI and ARDS. *Adv Chronic Kidney Dis*, 20(1):14-20, 2013.

Seif-Naraghi et al., *Sci Transl Med.*, 5(173):173ra25, 2013.

Sharma et al., *The Journal of antimicrobial chemotherapy*, 54, (4), 761-6, 2004.

Sokocevic et al. *Biomaterials.*, 34:3256-69, 2013.

Suga et al., Disruption of the klotho gene causes pulmonary emphysema in mice. Defect in maintenance of pulmonary integrity during postnatal life. *Am J Respir Cell Mol Biol*, 22(1):26-33, 2000.

Sung et al., *Trends in biotechnology* 25, (12), 563-70, 2007.

Syedain et al., *Tissue engineering. Part A*, 19, (5-6), 759-69, 2013.

Tahara et al., *International journal of pharmaceutics*, 382, (1-2), 198-204, 2009.

Takenaga et al., 1998.

Tanito et al., Upregulation of thioredoxin system via Nrf2-antioxidant responsive element pathway in adaptive-retinal neuroprotection in vivo and in vitro. *Free Radic Biol Med*, 42(12):1838-1850, 2007.

Thimmulappa et al., Nrf2-dependent protection from LPS induced inflammatory response and mortality by CDDO-Imidazolide. *Biochem Biophys Res Commun*, 351(4):883-889, 2006.

Tsushima et al., *Internal medicine*, 48, (9), 621-30, 2009.

Volpato et al., *Biomaterials*, 34, (21), 4945-55, 2013.

Wolf et al., *Biomaterials*, 33(29):7028-38, 2012.

Wu J et al. *Acta Biomater.*, 16:49-59, 2015.

Yamamoto et al., *Journal of controlled release: official journal of the Controlled Release Society*, 102, (2), 373-81, 2005.

Yamamoto et al., Regulation of oxidative stress by the anti-aging hormone klotho. *J Biol Chem*, 280(45):38029-38034, 2005.

Yap and Lee, Acute kidney injury and extrarenal organ dysfunction: new concepts and experimental evidence. *Anesthesiology*, 116(5):1139-1148, 2012.

Zeldich et al., The neuroprotective effect of Klotho is mediated via regulation of members of the redox system. *J Biol Chem*, 289(35):24700-24715, 2014.

Zanen et al. The optimal particle size for beta-2-adrenergic aerosols in mild asthmatics. *Int J Pharm*, 107:211-217, 1994.

Zanen et al. "Optimal particle size for b2-agonist and anticholinergic aerosols in patients with severe airflow obstruction." *Thorax*, 51: 977±980, 1996.

What is claimed is:

1. A method comprising administering a pharmaceutical preparation comprising a plurality of nanoparticles to a subject via inhalation or aerosol delivery, wherein the nanoparticles contain a drug, wherein the drug consists of an α-Klotho protein or is a nucleic acid encoding a protein consisting of α-Klotho; wherein the subject has a lung disease which is an acute lung injury (ALI) or acute respiratory distress syndrome (ARDS), and wherein the lung disease is characterized by oxidative damage or oxidative stress.

2. The method of claim 1, wherein the disease is an acute lung injury.

3. The method of claim 1, wherein an exterior surface of the nanoparticles comprises or is at least partially coated with a decellularized extracellular matrix (ECM).

4. The method of claim 3, wherein the extracellular matrix comprises or consists of decellularized lung tissue.

5. The method of claim 4, wherein the decellularized lung tissue is decellularized porcine lung tissue.

6. The method of claim 1, wherein the nanoparticles comprise poly(lactic-co-glycolic) (PLGA), poly(lactic acid) (PLA), poly(glycolic acid) (PGA), gelatin, chitosan, liposome, or a combination thereof.

7. The method of claim 6, wherein the nanoparticles are PLGA nanoparticles.

8. The method of claim 3, wherein the nanoparticles are coated with the extracellular matrix.

9. The method of claim 8, wherein the nanoparticles are generated via a single or double emulsion method.

10. The method of claim 8, wherein the extracellular matrix is coated on the nanoparticles layer by layer or via physical adsorption.

11. The method of claim 1, wherein the subject is a human.

12. The method of claim 1, wherein the disease is an acute respiratory distress syndrome.

* * * * *

SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
tctcttggct ggcttcctta                                          20

<210> SEQ ID NO 2
<211> LENGTH: 20
<212> TYPE: DNA
<213> ORGANISM: Artificial Sequence

```
-continued

<220> FEATURE:
<223> OTHER INFORMATION: Synthetic Primer

<400> SEQUENCE: 2
attgcctgga tgtgcttttc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
gaaggaaggg accaaggaag                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
gtggccagct taaacagctc                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
ggcaaaggtg gaaatgaaga                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gggcctcaga ctacatccaa                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
gcctcctaca tcctcatgga                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
aaagatgccc agctctgaaa                                              20
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
gcaaatgcaa agagtgcaaa                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
cagctgcact tctctgatgc                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
caacctgtcc cgactctagc                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
aggagcagca gcttttcttg                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
agagaggaag gcaggtgtca                                                20

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
ctggacttcc tgcttcttgg                                                20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer
```

<400> SEQUENCE: 15
aacggtgcct cgagtcttta                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
caattgggtc ctgtgacctt                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
gccattgtca aacctggagt                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
aacgtagcgt agcctttgga                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
gcttcaaatg gcagaaaagc                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer

<400> SEQUENCE: 20
agaacccatc gaccatcaag                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
tggggtctta aaggctgatg                                               20

```
<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
tccccatgtt tgtcagtgaa                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
gtgtccttcg ccagatcact                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
acgttgggct taatcgtgtc                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
gccgttgtca atggagagtt                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26
tccactgaga ctgcgacaac                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
acggtgcagt gaaggagagt                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic Primer
```

```
<400> SEQUENCE: 28
aacagctctg ccaggttcac                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic Primer

<400> SEQUENCE: 29
ggatggggat agtgtgatgg                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic Primer

<400> SEQUENCE: 30
ctgacatcct ctggctcaca                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic Primer

<400> SEQUENCE: 31
cacagagcac ttgcggttta                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic Primer

<400> SEQUENCE: 32
gcaggctctg gctcaaatac                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer

<400> SEQUENCE: 33
agaggggctg aagcacatta                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer

<400> SEQUENCE: 34
caggttggcc tgaagacact                                               20
```

```
<210> SEQ ID NO 35
<211> LENGTH: 20
<212> TYPE: DNA
<213> ORGANISM: Artificial Sequence
<220> FEATURE:
<223> OTHER INFORMATION: Synthetic Primer

<400> SEQUENCE: 35
tgtggctcct gagttgagtg                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic Primer

<400> SEQUENCE: 36
tcaatctgct ccatgctacg                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic Primer

<400> SEQUENCE: 37
ttgcgactgg actcaaacac                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic Primer

<400> SEQUENCE: 38
ggcctttcac agttcagctc                                               20
```